(12) United States Patent
Saito et al.

(10) Patent No.: US 8,951,240 B2
(45) Date of Patent: Feb. 10, 2015

(54) FLEXIBLE TUBE FOR ENDOSCOPE AND ENDOSCOPE

(71) Applicant: Olympus Medical Systems Corp., Tokyo (JP)

(72) Inventors: Kenichiro Saito, Tachikawa (JP); Takahiro Kishi, Yokohama (JP); Mamoru Machiya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/143,696

(22) Filed: Dec. 30, 2013

(65) Prior Publication Data

US 2014/0188081 A1 Jul. 3, 2014

Related U.S. Application Data

(63) Continuation of application No. PCT/JP2013/061864, filed on Apr. 23, 2013.

(30) Foreign Application Priority Data

May 11, 2012 (JP) ................................. 2012-109773

(51) Int. Cl.
*A61B 1/005* (2006.01)
*A61B 1/00* (2006.01)

(52) U.S. Cl.
CPC .............. *A61B 1/005* (2013.01); *A61B 1/00073* (2013.01); *A61B 1/00078* (2013.01); *A61B 1/00135* (2013.01)
USPC ......................................... 604/525; 600/139

(58) Field of Classification Search
CPC .......... A61B 1/00135; A61B 1/00142; A61M 25/0054; A61M 25/0053; A61M 25/0012; A61M 25/005; A61M 25/0045
USPC .......... 604/525–527; 600/121, 139, 140–141, 600/143–144
See application file for complete search history.

(56) References Cited

U.S. PATENT DOCUMENTS

2002/0010386 A1* 1/2002 Matsushita et al. ........... 600/140

FOREIGN PATENT DOCUMENTS

| JP | Y-49-29112 | 8/1974 |
|---|---|---|
| JP | U1-53-111592 | 9/1978 |
| JP | A-58-103431 | 6/1983 |
| JP | A-5-56910 | 3/1993 |
| JP | A-5-95895 | 4/1993 |
| JP | A-2003-19109 | 1/2003 |

OTHER PUBLICATIONS

International Search Report issued in Application No. PCT/JP2013/061864 mailed May 21, 2013 (with translation).

* cited by examiner

*Primary Examiner* — Nicholas Lucchesi
*Assistant Examiner* — Melissa A Snyder
(74) *Attorney, Agent, or Firm* — Oliff PLC

(57) ABSTRACT

A flexible tubular portion for an endoscope having a central axis includes a spiral tube, an outer layer covering the outside of the spiral tube, and an inhibiting portion. The spiral tube includes, along the longitudinal direction of the central axis, a closely wound portion to which an initial tension is applied, and sparsely wound portions provided on the distal side and the proximal side of the closely wound portion. The inhibiting portion inhibits the movement of at least a part of the sparsely wound portions relative to the outer layer in the longitudinal direction of the spiral tube.

20 Claims, 25 Drawing Sheets

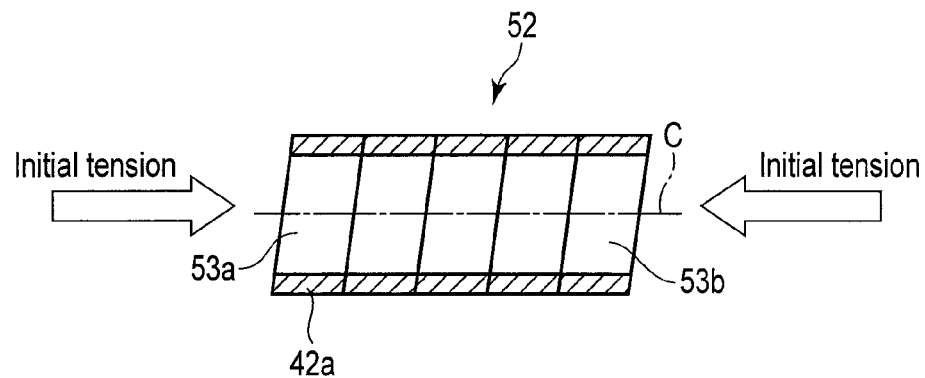
F I G. 5A
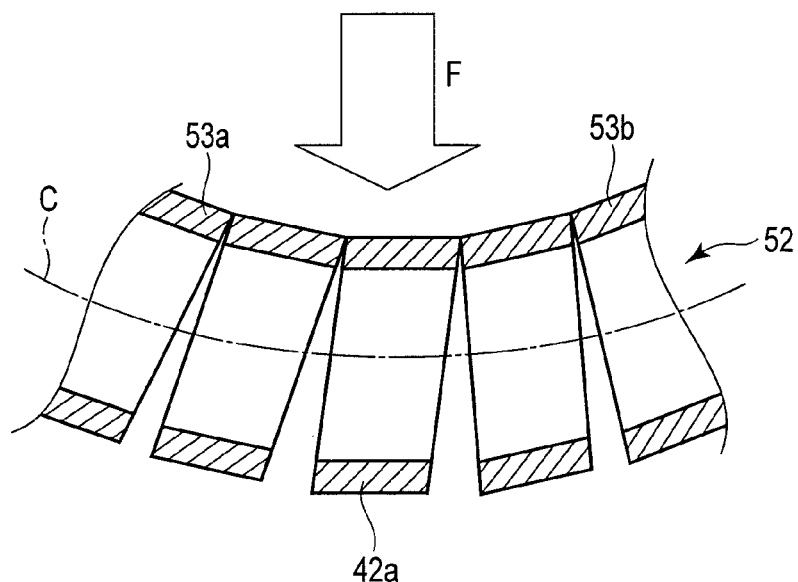
F I G. 5B

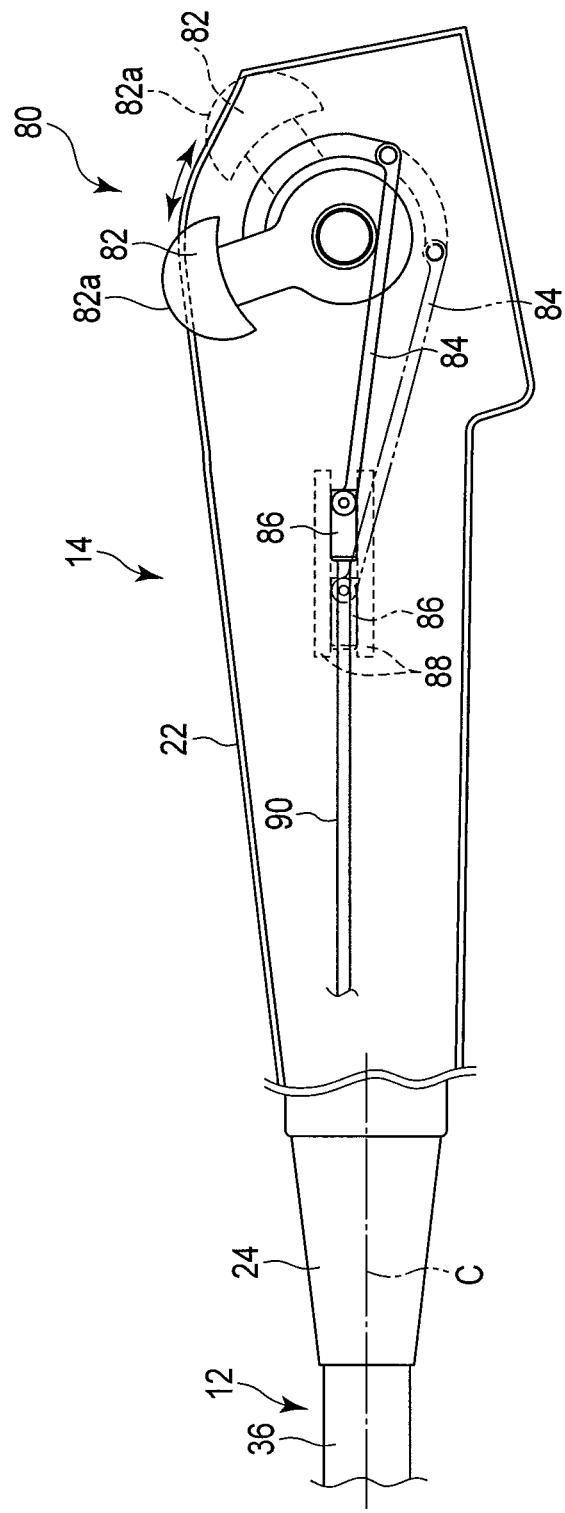
F I G. 8A

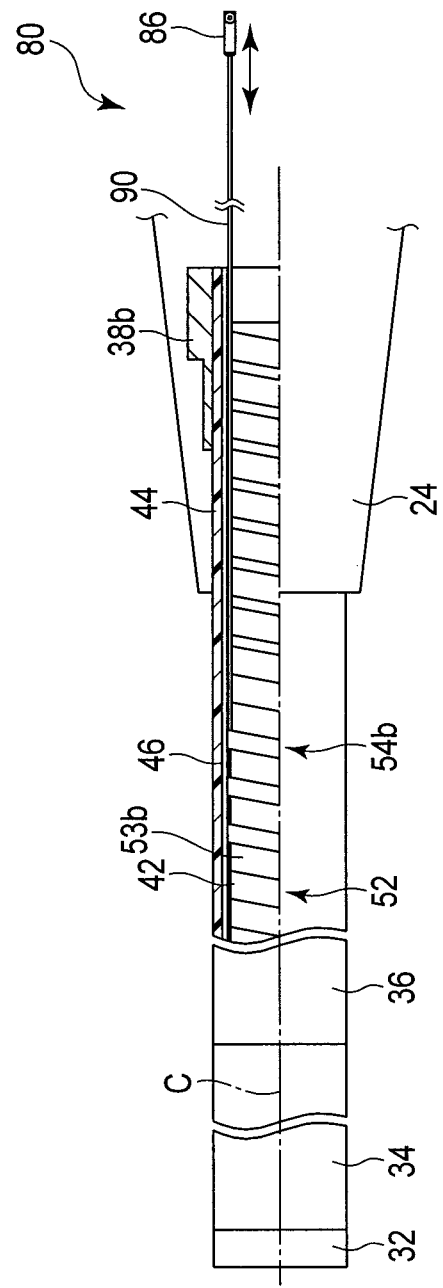
F I G. 8B

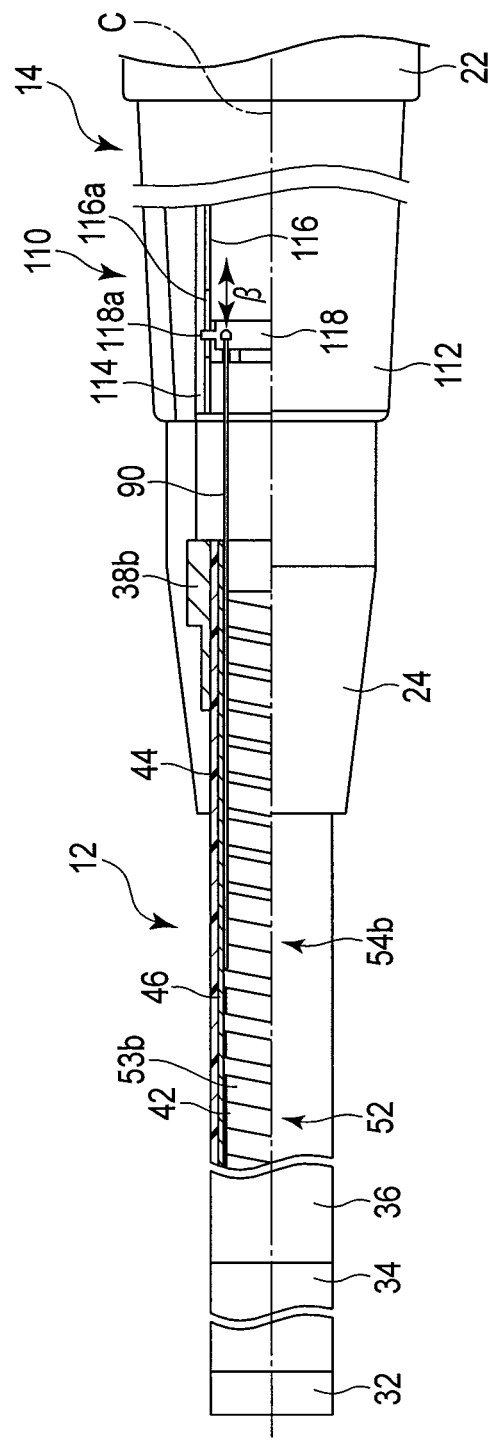
F I G. 9A

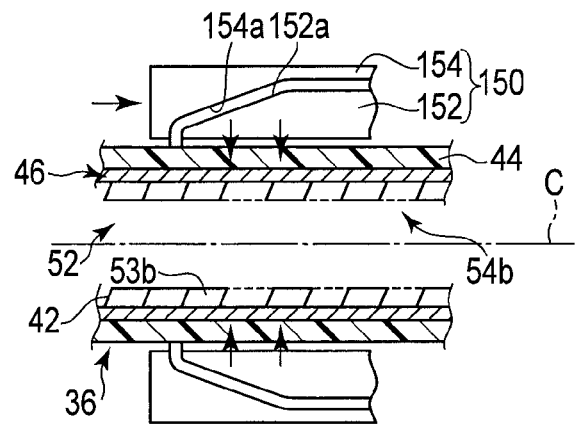
F I G. 11
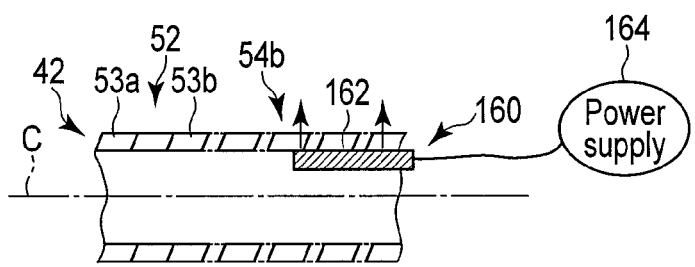
F I G. 12A
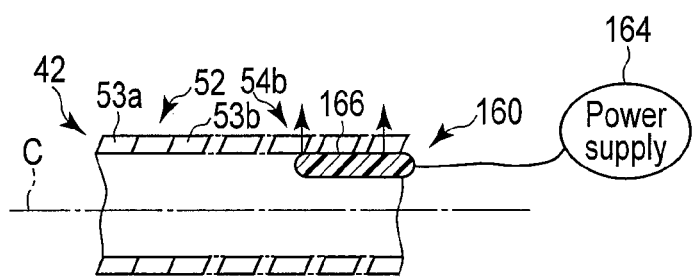
F I G. 12B

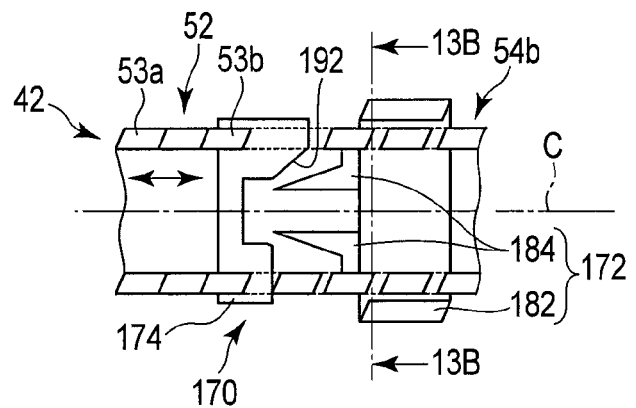
F I G. 13A
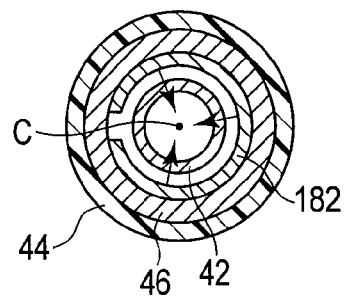
F I G. 13B
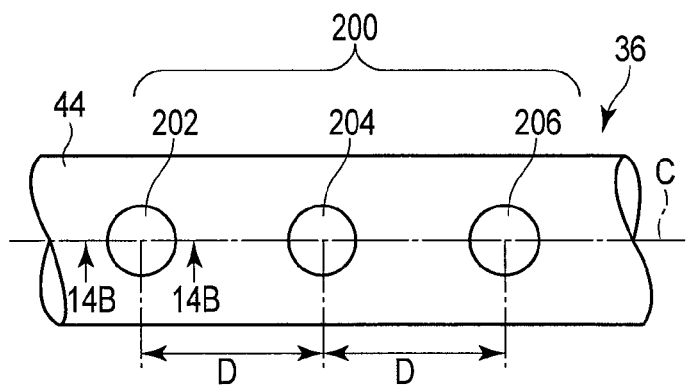
F I G. 14A

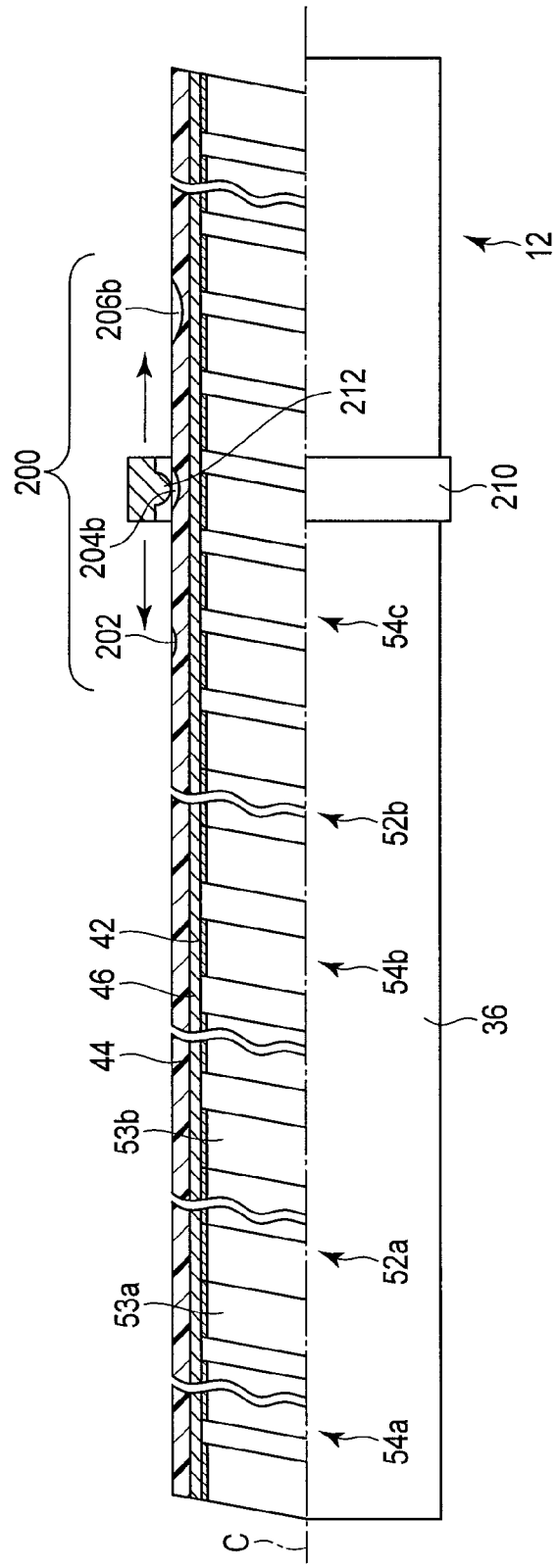
F I G. 15B

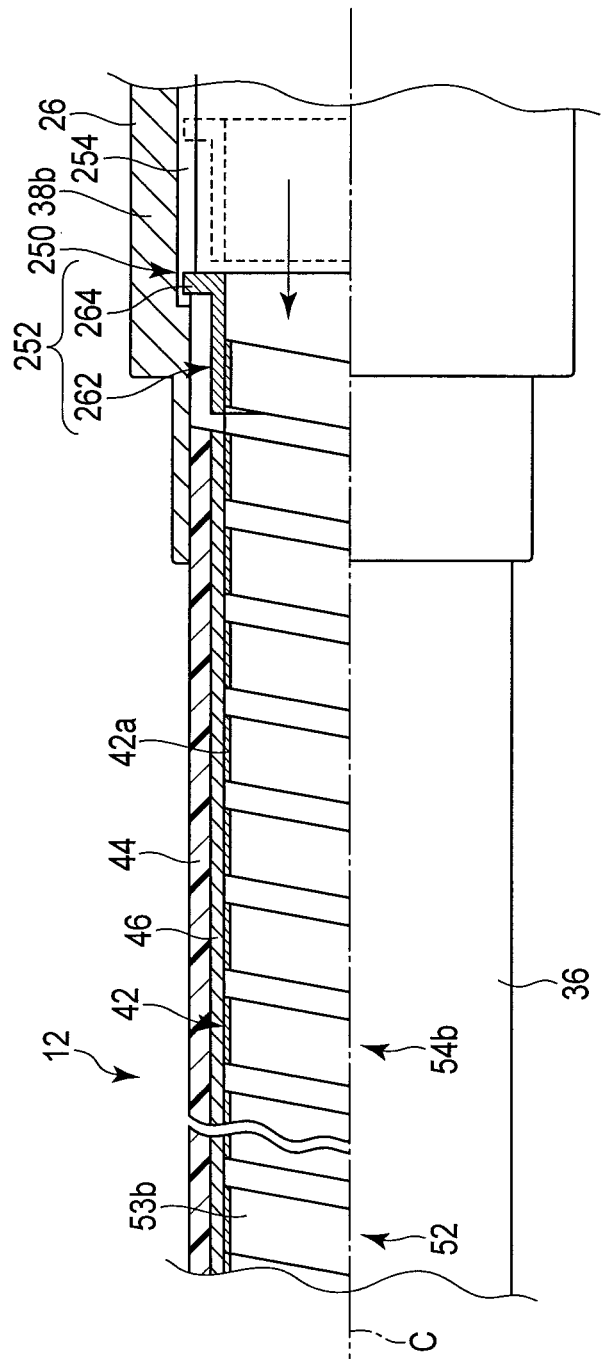
F I G. 19A

FLEXIBLE TUBE FOR ENDOSCOPE AND ENDOSCOPE

CROSS-REFERENCE TO RELATED APPLICATIONS

This is a Continuation Application of PCT Application No. PCT/JP2013/061864, filed Apr. 23, 2013, which was published under PCT Article 21(2) in Japanese.

This application is based upon and claims the benefit of priority from the prior Japanese Patent Application No. 2012-109773, filed May 11, 2012, the entire contents of which are incorporated herein by reference.

BACKGROUND OF THE INVENTION

1. Field of the Invention

This invention relates to a flexible tube for endoscope for use in an insertion portion to be inserted into a lumen, and an endoscope including the endoscopic flexible tube.

2. Description of the Related Art

For example, according to Jpn. Pat. Appln. KOKAI Publication No. 2003-19109, a variable-pitch spiral tube is provided in a flexible tube to adjust the flexibility (bendability) of the flexible tube of an insertion portion. The spiral tube is located inside the flexible tube out of alignment with its central axis. The flexibility of the flexible tube can be changed by narrowing or expanding the pitch of the spiral tube.

BRIEF SUMMARY OF THE INVENTION

According to one aspect of the invention, a flexible tubular portion for an endoscope having a central axis includes: a spiral tube including, along the longitudinal direction of the central axis, a closely wound portion to which an initial tension is applied, and sparsely wound portions provided on the distal side and the proximal side of the closely wound portion, an outer layer covering the outside of the spiral tube; and an inhibiting portion which inhibits the movement of at least a part of the sparsely wound portions relative to the outer layer in the longitudinal direction of the spiral tube.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5A is a schematic longitudinal sectional view showing how an initial tension is applied to the closely wound portion of the spiral tube of the flexible tubular portion of the insertion portion in the endoscope according to the first to third embodiments so that the closely wound portion is kept straight;

FIG. 5B is a schematic longitudinal sectional view showing how the closely wound portions are deformed when force is applied laterally relative to the central axis of the closely wound portion;

FIG. 8A is a schematic longitudinal sectional view showing the structure of a lever adjusting portion provided in the operation portion of the endoscope according to the first embodiment;

FIG. 8B is a schematic partial longitudinal sectional view showing how a second spiral tube moves relative to the sparsely wound portion on the proximal side of a first spiral tube in response to the movement of a movable rod associated with the movement of a lever of the lever adjusting portion;

FIG. 9A is a schematic partial longitudinal sectional view showing the structure of a cam ring adjusting portion provided in the operation portion of the endoscope according to a first modification of the first embodiment;

FIG. 11 is a schematic partial longitudinal sectional view showing a catching portion provided in the flexible tubular portion of the insertion portion in the endoscope according to a fourth modification of the first embodiment;

FIG. 12A is a schematic longitudinal sectional view showing an actuator mechanism having a piezoelectric element provided inside the spiral tube of the flexible tubular portion of the insertion portion in the endoscope according to a fifth modification of the first embodiment;

FIG. 12B is a schematic longitudinal sectional view showing an artificial muscle having flexibility instead of the piezoelectric element;

FIG. 13A is a schematic longitudinal sectional view showing a C-ring fastening mechanism provided in the spiral tube of the flexible tubular portion of the insertion portion in the endoscope according to a fifth modification of the first embodiment;

FIG. 13B is a schematic cross sectional view taken along the line 13B-13B in FIG. 13A;

FIG. 14A is a schematic front view showing the outer circumferential surface of the flexible tubular portion in the insertion portion of the endoscope according to a second embodiment;

FIG. 15B is a schematic partial longitudinal sectional view showing depressions in the flexible tubular portion of the insertion portion in the endoscope according to a third modification of the second embodiment, and showing a press member for pressing the depressions;

FIG. 19A is a schematic partial longitudinal sectional view showing the proximal end of the flexible tubular portion having the three-layer structure of the insertion portion, and the protection hood of the operation portion in the endoscope according to the third embodiment.

DETAILED DESCRIPTION OF THE INVENTION

Hereinafter, embodiments of this invention will be described with reference to the drawings.

First Embodiment

A first embodiment is described with reference to FIG. 1 to FIG. 13B.

Figure 1:
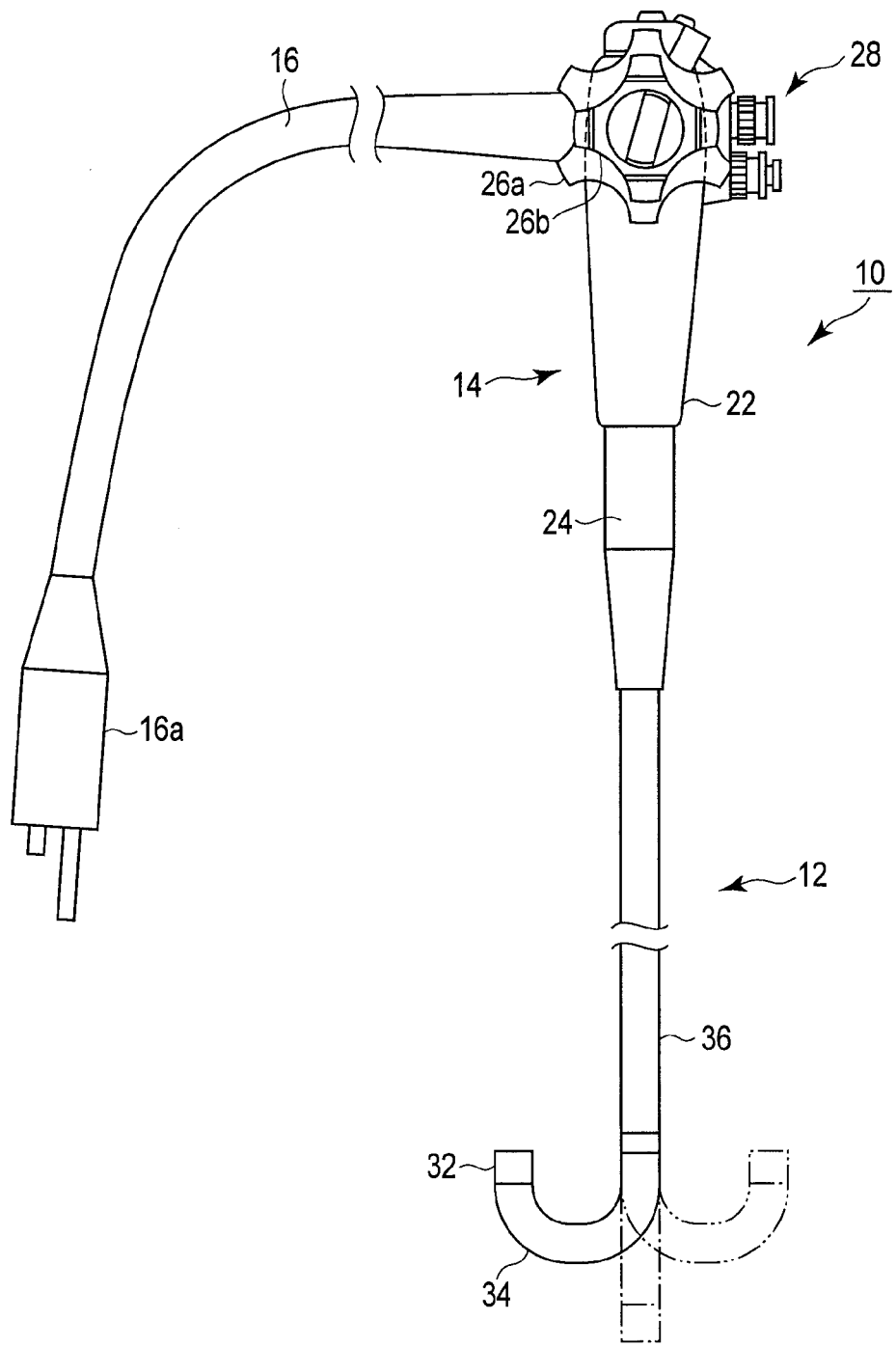
FIG. 1 is a schematic diagram of an endoscope according to first to third embodiments.

As shown in FIG. 1, an endoscope 10 according to this embodiment includes an elongated insertion portion 12 to be inserted into a lumen such as a body cavity of a patient, an operation portion 14 coupled to the proximal portion of the insertion portion 12, and a universal cable 16 extending from the operation portion 14. A connector 16a connected to, for example, a light source device and a processor is provided at the end of the universal cable 16.

The operation portion 14 has a main body 22 held by a user, a protection hood 24 which fixes the proximal end of the insertion portion 12 (the proximal end of a flexible tubular portion 36), bending operation knobs 26a and 26b, and various switches 28. The protection hood 24 is provided between the proximal end of the insertion portion 12 and the main body 22 of the operation portion 14. The bending operation knobs 26a and 26b and the various switches 28 are located in the vicinity of the universal cable 16.

The insertion portion 12 has, on its central axis C, a distal hard portion 32, a bending portion 34, and the flexible tubular portion (endoscopic flexible tubular portion) 36, from the distal side to the proximal side. The proximal portion of the distal hard portion 32 is coupled to the distal portion of the bending portion 34, and the proximal portion of the bending portion 34 is coupled to the distal portion of the flexible tubular portion 36 by a mouth ring 38a. The proximal end of the flexible tubular portion 36 is fixed to a mouth ring 38b (see FIG. 7 and FIG. 8B), and supported so that the mouth ring 38b cannot move into the protection hood 24 of the operation portion 14.

The distal hard portion 32 has a hard columnar body (not shown) made of, for example, stainless steel, and an insulating tubular outer tube (an outer tube 34b of the bending portion 34) covering the outer circumference of the body. The distal ends of, for example, an illumination optical system, an observation optical system, an air/water supply tube, and a forceps channel which are not shown and which are provided inside the insertion portion 12 are fixed to the body.

Figure 2:
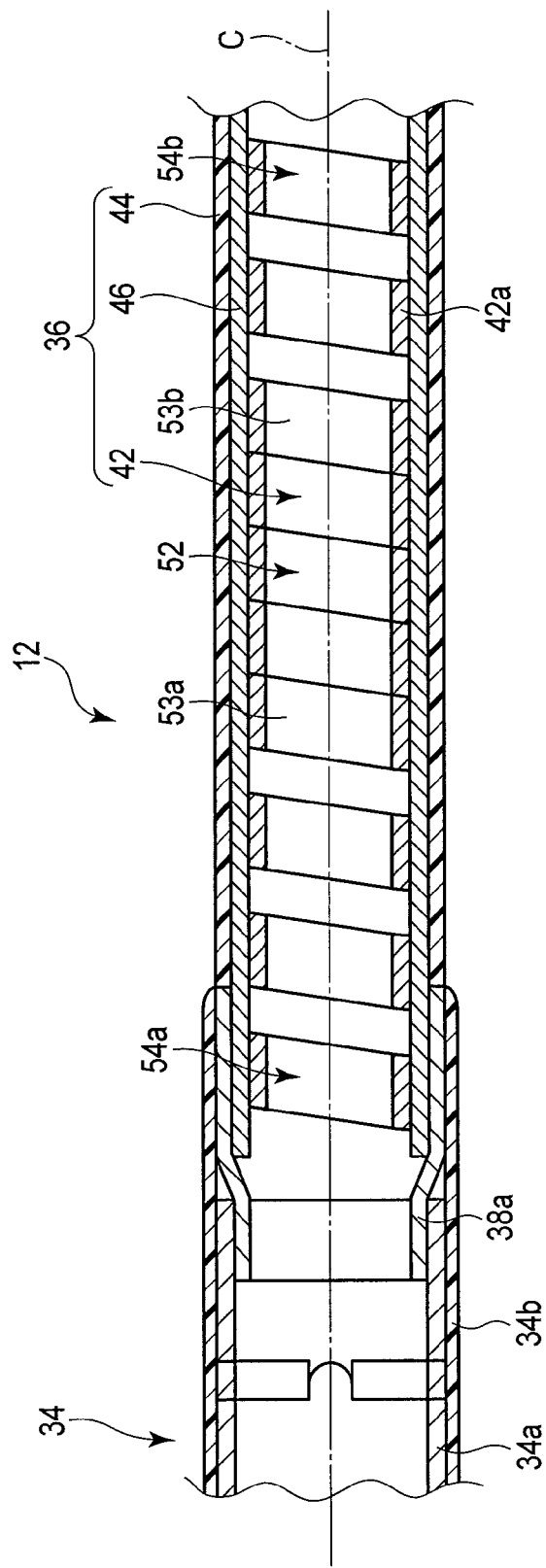
FIG. 2 is a schematic longitudinal sectional view showing a bending portion and a flexible tubular portion having a three-layer structure of an insertion portion of the endoscope according to the first to third embodiments.
Figure 3A:
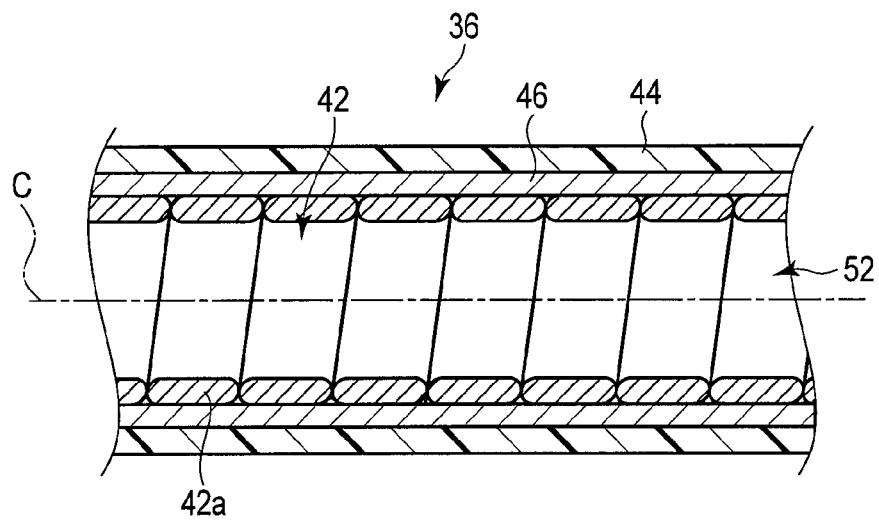
FIG. 3A is a schematic longitudinal sectional view showing an oval shaped longitudinal section of a linear member of the flexible tubular portion having the three-layer structure of the insertion portion in the endoscope according to the first to third embodiments.
Figure 3B:
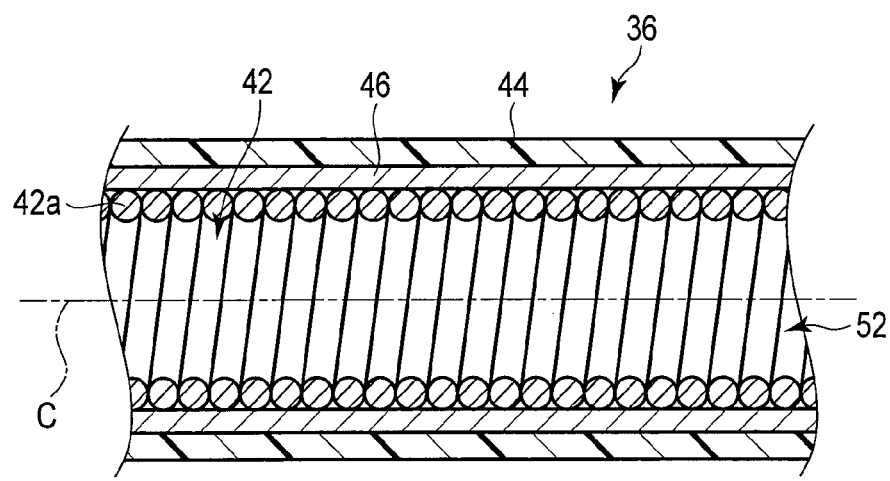
FIG. 3B is a schematic longitudinal sectional view showing a circularly shaped longitudinal section of the linear member of the flexible tubular portion having the three-layer structure of the insertion portion in the endoscope according to the first to third embodiments.
Figure 3C:
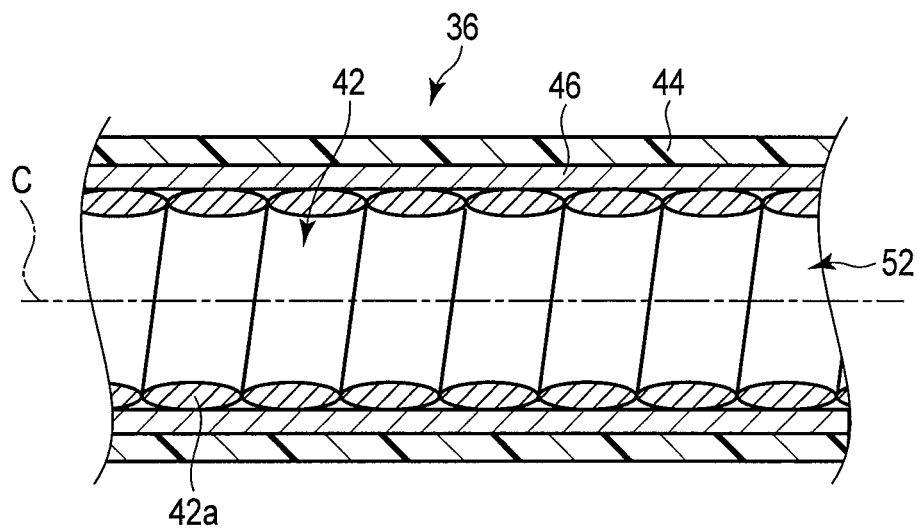
FIG. 3C is a schematic longitudinal sectional view showing an elliptically shaped longitudinal section of the linear member of the flexible tubular portion having the three-layer structure of the insertion portion in the endoscope according to the first to third embodiments.

As shown in FIG. 2, the bending portion 34 has a bending tube 34a which is preferably capable of bending in four directions relative to the central axis C of the insertion portion 12, and the outer tube 34b covering the bending tube 34a. The bending tube 34a of the bending portion 34 is remotely operated by the bending operation knobs 26a and 26b in which unshown one or two pairs of (multiple pairs of) wires (inner objects) that are inserted through a later-described spiral tube (flex) 42 of the flexible tubular portion 36 are provided in the operation portion 14. That is, the bending portion 34 is bent in a desired direction at the distal portion of the flexible tubular portion 36 by the operation of the bending operation knobs 26a and 26b of the operation portion 14. When a pair of wires is inserted through the spiral tube 42, the bending portion 34 can be bent in two directions: an upward (U) direction and a downward (D) direction. When two pairs of wires are inserted through the spiral tube 42, the bending portion 34 can be curved in a total of four directions: two directions including a leftward (L) direction and a rightward (R) direction as well as two directions including the upward (U) direction and the downward (D) direction.

The flexible tubular portion 36 according to this embodiment is hollow and has desired flexibility, and is bent when receiving external force F from a direction that deviates from the central axis (the central axis of the insertion portion 12) C of the flexible tubular portion 36. The flexible tubular portion 36 according to this embodiment comprises the spiral tube (first spiral tube) 42, and an outer tube (outer layer) 44 covering the outer circumference of the spiral tube 42. It is also preferable that a mesh tube (braid) 46 as the outer layer of the spiral tube 42 is provided between the spiral tube 42 and the outer tube 44. Although the flexible tubular portion 36 preferably has a three-layer structure including the spiral tube 42, the mesh tube 46, and the outer tube 44, the mesh tube 46 does not necessarily have to be provided. That is, it is also preferable that the flexible tubular portion 36 has a two-layer structure including the spiral tube 42 and the outer tube 44.

The spiral tube 42 is formed by spirally winding, for example, stainless steel linear member 42a. That is, the spiral tube 42 is shaped like a coil pipe. Various shapes of the cross section of the linear member 42a are permitted; for example, a rectangular shape shown in FIG. 2, an oval shape shown in FIG. 3A, a substantially circular shape shown in FIG. 3B, and an elliptic shape shown in FIG. 3C. In this embodiment described below, the cross section has the rectangular shape shown in FIG. 2.

The outer tube 44 is formed by a thermoplastic elastomer such as polyurethane or polyester, and its outer coat layer. The mesh tube 46 is formed by woven bundles of wires.

The spiral tube 42 is a helical tubular member having elastic force. As shown in FIG. 2, the spiral tube 42 integrally has a closely wound portion 52 to which an initial tension is applied along the longitudinal direction of the central axis C, and sparsely wound portions 54a and 54b provided at both ends of the closely wound portion 52. That is, the spiral tube 42 has the sparsely wound portion 54a, the closely wound portion 52, and the sparsely wound portion 54b in order from the distal end to the proximal end. The closely wound portion 52 has a distal portion 53a and a proximal portion 53b. The distal portion 53a is integrally joined to the one sparsely wound portion 54a, and the proximal portion 53b is integrally joined to the other sparsely wound portion 54b. Thus, the closely wound portion 52 is held between the sparsely wound portions 54a and 54b along the central axis C of the spiral tube 42, and is adjacent to the sparsely wound portions 54a and 54b in the distal portion 53a and the proximal portion 53b.

Since the spiral tube 42 has elastic force such as spring characteristics, the closely wound portion 52 is produced by, for example, a solid coil spring, and the sparsely wound portions 54a and 54b are produced by, for example, sparsely wound coil springs. That is, the closely wound portion 52 is formed by, for example, a solid coil, and the sparsely wound portions 54a and 54b are formed by, for example, sparsely wound coils. The distance between the distal end of the closely wound portion 52 and the proximal end of the bending portion 34 is formed to be smaller than the distance between the proximal end of the closely wound portion 52 and the operation portion 14. That is, the closely wound portion 52 is preferably located closer to the bending portion 34 than the operation portion 14.

Figure 4:
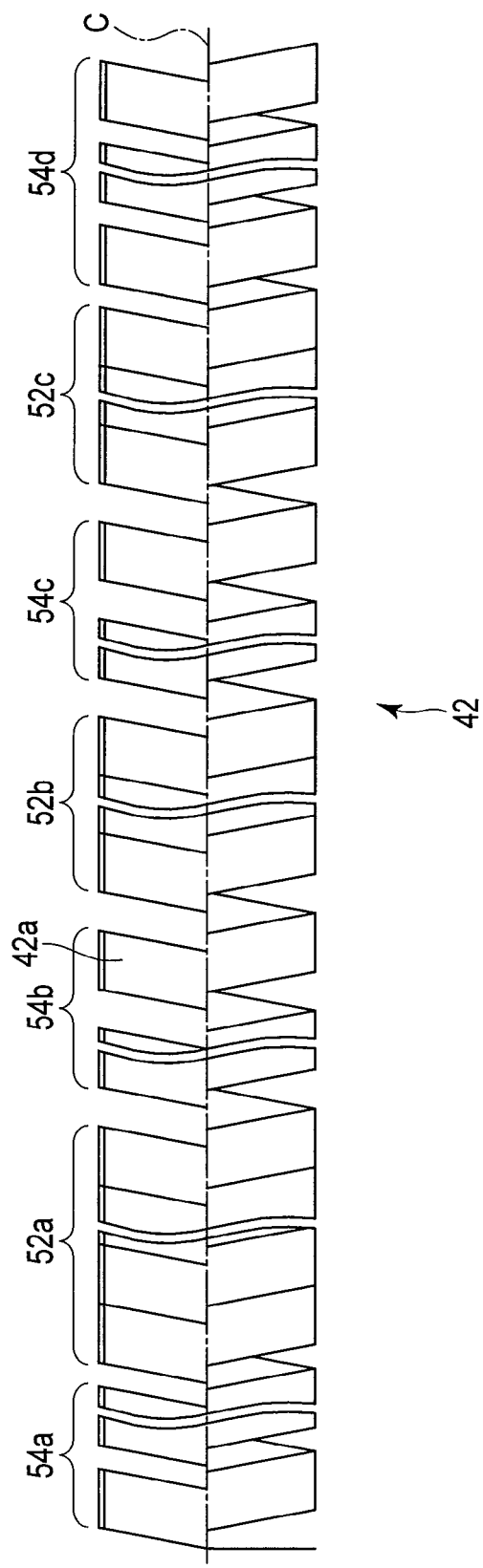
FIG. 4 is a schematic partial longitudinal sectional view showing a spiral tube of the flexible tubular portion of the insertion portion in the endoscope according to the first to third embodiments, and particularly showing the spiral tube having a plural place of closely wound portions and a plural place of sparsely wound portions.

Although one closely wound portion 52 is included in the spiral tube 42 in the example described according to this embodiment, multiple (e.g., two to three) closely wound portions 52 may be included in the spiral tube 42 as shown in FIG. 4. When three closely wound portions 52 are included, the spiral tube 42 is structured to have the sparsely wound portion 54a, a closely wound portion 52a, the sparsely wound portion 54b, a closely wound portion 52b, a sparsely wound portion 54c, a closely wound portion 52c, and a sparsely wound portion 54d from the distal side to the proximal side.

As shown in FIG. 2, the spiral tube 42 having the closely wound portion 52 and the sparsely wound portions 54a and 54b is formed by spirally winding the linear member (wire) 42a. The closely wound portion 52 and the sparsely wound portions 54a and 54b are integrally formed by the same linear member 42a.

Here, the initial tension applied to the closely wound portion 52 of the spiral tube 42 used in this embodiment is described.

As shown in FIG. 5A, the initial tension refers to a force which works in a direction to bring the edges of the linear members 42a of the closely wound portion 52 into close contact with each other. In other words, when the central axis C of the closely wound portion 52 is, for example, horizontally placed, the initial tension refers to the force (preload) which keeps the edges of the linear members 42a of the closely wound portion 52 in close contact with each other and keeps the closely wound portion 52 difficult to bend and substantially straight against the external force (e.g., gravity) F. When the central axis C of the closely wound portion 52 is, for example, vertically placed, the initial tension refers to a force (preload) which keeps the edges of the linear members 42a of the closely wound portion 52 in close contact with each other against gravity and keeps no space between the linear members 42a.

For example, as shown in FIG. 5A, the external force F is applied to the central axis C of the closely wound portion 52 when the central axis C is, for example, horizontally placed. In this case, until the external force reaches a force that cancels the initial tension, no space is formed between the linear members 42a, and the closely wound portion 52 is not bent. On the other hand, when the external force F applied to the central axis C becomes equal to or more than the force that cancels the initial tension as shown in FIG. 5B, a space is formed between the linear members 42a that have been in close contact, and the closely wound portion 52 is bent.

Therefore, flexural rigidity is high because of the initial tension applied to the closely wound portion 52 until the closely wound portion 52 starts bending. After the closely wound portion 52 starts bending and the initial tension is canceled, the closely wound portion 52 is bent in accordance with the spring constant of the spiral tube 42. Therefore, when the insertion portion 12 is inserted into a lumen such as the large intestine, once the closely wound portion 52 of the flexible tubular portion 36 starts bending, the flexible tubular portion 36 can be bent as if the closely wound portion 52 were not present.

This initial tension is applied when the spiral tube 42 is formed, that is, when the closely wound portion 52 is formed. The initial tension applied in this case can be properly adjusted, for example, by the winding degree of the linear member 42a.

Here, as shown in FIG. 2, the distal end of the spiral tube 42 is fixed to the mouth ring 38a, and the proximal end of the spiral tube 42 is fixed to the inside of the operation portion 14. The axial length of the cylindrical outer tube 44 along the central axis C is substantially invariable and substantially the same whether the outer tube 44 is straight or bent. Accordingly, the length of the central axis C of the spiral tube 42 covered by the outer tube 44 is also substantially invariable and substantially the same whether the spiral tube 42 is straight or bent. Thus, as shown in FIG. 5B, the overall length of the spiral tube 42 hardly changes even when the spiral tube 42 receives the external force F from the direction that deviates from the central axis C of the flexible tubular portion 36.

Figure 6A:
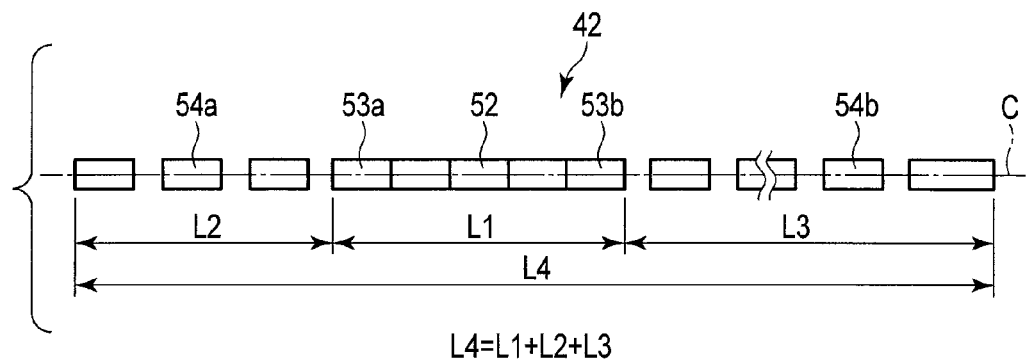
FIG. 6A is a schematic diagram showing the relation between the length of the spiral tube, the length of the sparsely wound portion, and the length of the closely wound portion when the spiral tube of the flexible tubular portion of the insertion portion in the endoscope according to the first to third embodiments is straight.

As shown in FIG. 6A, in the axial direction of the straight spiral tube 42, the length of the closely wound portion 52 in a direction along the central axis C is L1, the length of the one sparsely wound portion 54a in the direction along the central axis C is L2, the length of the other sparsely wound portion 54b in the direction along the central axis C is L3, and the length of the spiral tube 42 along the central axis C is L4, $$L4=L1+L2+L3 \qquad \text{Equation (1).}$$

Figure 6B:
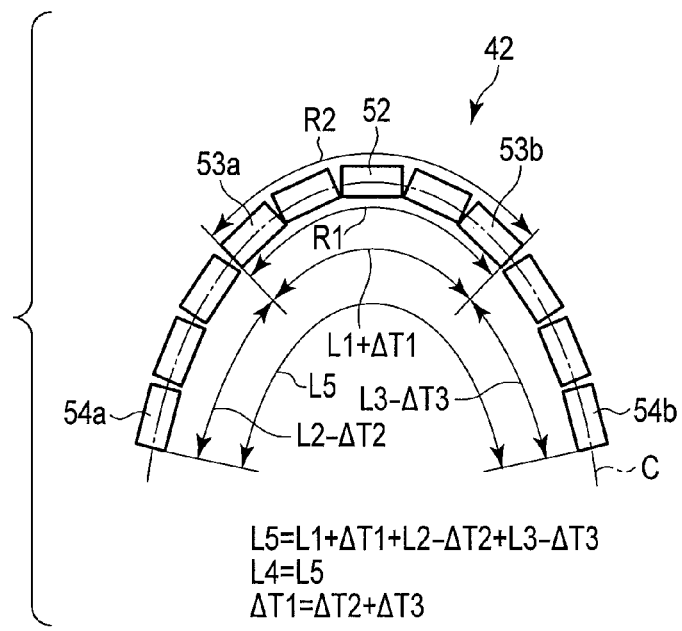
FIG. 6B is a schematic diagram showing the relation between the length of the spiral tube, the length of the sparsely wound portion, and the length of the closely wound portion when the spiral tube is bent.

If the spiral tube 42 is bent from the state shown in FIG. 6A by the application of the external force F from the direction that deviates from the central axis C of the spiral tube 42, the linear members 42a in an inner arc-shaped portion R1 are kept in abutment with each other by the initial tension relative to the central axis C of the closely wound portion 52 of the spiral tube 42, and the linear members 42a in an outer arc-shaped portion R2 are separated from each other relative to the central axis C of the closely wound portion 52, as shown in FIG. 6B. Accordingly, the length of the central axis C of the closely wound portion 52 increases ΔT1 in total. That is, when the closely wound portion 52 is bent, the axial length of the central axis C of the closely wound portion 52 is L1+ΔT1.

The axial length of the central axis C of the closely wound portion 52 of the spiral tube 42 is ΔT1 greater when the closely wound portion 52 is bent (see FIG. 6B) than when the closely wound portion 52 is straight (see FIG. 6A). In the present embodiment, the sparsely wound portions 54a and 54b are provided so that the closely wound portion 52 is held in between. Thus, as shown in FIG. 6A and FIG. 6B, when the closely wound portion 52 is bent, the edges of the linear members 42a in the direction along the central axis C of the distal-side (one) sparsely wound portion 54a are closer to each other than when the sparsely wound portion 54a is straight. That is, when the closely wound portion 52 is bent, the space between the edges of the linear members 42a is smaller in the distal-side sparsely wound portion 54a. Thus, the axial length of the distal-side sparsely wound portion 54a along the central axis C is ΔT2 smaller than when the sparsely wound portion 54a is straight. That is, when the closely wound portion 52 is bent, the axial length of the distal-side sparsely wound portion 54a along the central axis C is L2−ΔT2.

When the closely wound portion 52 is bent, the edges of the linear members 42a in the direction along the central axis C of the proximal-side (other) sparsely wound portion 54b are closer to each other than when the proximal-side sparsely wound portion 54b is straight. That is, when the closely wound portion 52 is bent, the space between the edges of the linear members 42a is smaller in the proximal-side sparsely wound portion 54b. Thus, the axial length of the proximal-side sparsely wound portion 54b along the central axis C is ΔT3 smaller than when the sparsely wound portion 54b is straight. That is, when the closely wound portion 52 is bent, the axial length of the other sparsely wound portion 54b along the central axis C is L3−ΔT3.

As shown in FIG. 6B, the length of the central axis of the bent spiral tube 42 is L5, $$L5=L1+\Delta T1+L2-\Delta T2+L3-\Delta T3 \qquad \text{Equation (2).}$$

Here, as described above, the length of the central axis of the spiral tube 42 needs to be invariable and remain the same whether the spiral tube 42 is straight or bent. That is, it is necessary that $$L4=L5 \qquad \text{Equation (3).}$$

If Equations (1) and (2) are substituted for Equation (3), $$L1+L2+L3=L1+\Delta T1+L2-\Delta T2+L3-\Delta T3 \text{, so that}$$
$$\Delta T1=\Delta T2+\Delta T3 \qquad \text{Equation (4).}$$

To put Equation (4) into words, the stretch amount of the closely wound portion 52="the contraction amount of the one sparsely wound portion 54a"+ "the contraction amount of the other sparsely wound portion 54b".

Thus, the stretch amount of the closely wound portion 52 is equal to the total of the contraction amounts of the sparsely wound portions 54a and 54b, and the sparsely wound portions 54a and 54b contract as much as the stretch amount of the closely wound portion 52. That is, the sparsely wound portions 54a and 54b absorb the stretch in the direction along the central axis C of the spiral tube 42 associated with the stretch in the direction along the central axis C of the closely wound portion 52 in the axial direction of the spiral tube 42 when the flexible tubular portion 36 is bent. Therefore, the sparsely wound portions 54a and 54b of the spiral tube 42 offset the stretch in the direction along the central axis C of the spiral tube 42. As a result, the flexible tubular portion 36 can be smoothly bent by the presence of the sparsely wound portions 54a and 54b so that the characteristics of the closely wound portion 52 having high spring characteristics as compared to the sparsely wound portions 54a and 54b are maintained.

When the insertion portion 12 is inserted into a body cavity (lumen) such as the large intestine, the user of the endoscope 10 generally holds the main body 22 of the operation portion 14 with the left hand, and presses the distal end of the insertion portion 12 into the body cavity while holding the flexible tubular portion 36 with the right hand.

For example, the flexible tubular portion 36 is inserted into a body cavity (lumen) such as the large intestine so that the flexible tubular portion 36 keeps straight at the position corresponding to the closely wound portion 52. In this case, when the external force (including gravity) F applied to the closely wound portion 52 from the direction that deviates from (e.g., the direction that intersects at right angles with) the direction of the spiral tube 42, for example, along the central axis C has not reached the force that cancels the initial tension, the closely wound portion 52 does not bend and keeps straight because of the high spring characteristics. Thus, the operation force amount of the flexible tubular portion 36 held by the user of the endoscope 10 with the right hand is transmitted to the distal portion of the flexible tubular portion 36 (the distal portion of the spiral tube 42) from the position where the flexible tubular portion 36 is held, and the flexible tubular portion 36 is more easily inserted into the body cavity. That is, the flexible tubular portion 36 at the position corresponding to the closely wound portion 52 can keep straight and is inserted into the lumen without bending.

When the external force (including gravity) F applied to the closely wound portion 52 of the flexible tubular portion 36 of the insertion portion 12 from the direction that deviates from (e.g., the direction that intersects at right angles with) the direction along the central axis C is equal to or more than the force that cancels the initial tension, the closely wound portion 52 starts bending against the high spring characteristics. If this external force F is applied, the distance (space) between the linear members 42a of the sparsely wound portions 54a and 54b of the spiral tube 42 is reduced.

Here, an inhibiting portion is formed to inhibit the movement of the sparsely wound portion 54b toward the spiral tube 42 by regulating the movement of at least some of the sparsely wound portions 54b of the spiral tube 42 relative to the outer layer covering the outer circumference of the spiral tube 42, that is, the outer tube 44 and the mesh tube 46. As a result, it is possible to control the distance between the linear members 42a of the sparsely wound portions 54a and 54b, that is, the contraction amount (movement amount) to adjust the degree of hardness (hardness) when the flexible tubular portion 36 is bent in the direction along the central axis C. Thus, the inhibiting portion is used as a hardness varying mechanism (hardness adjusting portion) of the flexible tubular portion 36.

Depending on the length of the flexible tubular portion 36 of the insertion portion 12, the inhibiting portion is preferably located, for example, in a range of 200 mm to 800 mm from the distal end of the spiral tube 42.

A structure (inhibiting portion) 70 described in this embodiment fastens all of the inner circumferential side or outer circumferential side of the sparsely wound portion 54b of the spiral tube 42 to prevent the sparsely wound portion 54b from moving relative to the outer tube 44 and the mesh tube 46.

Figure 7:
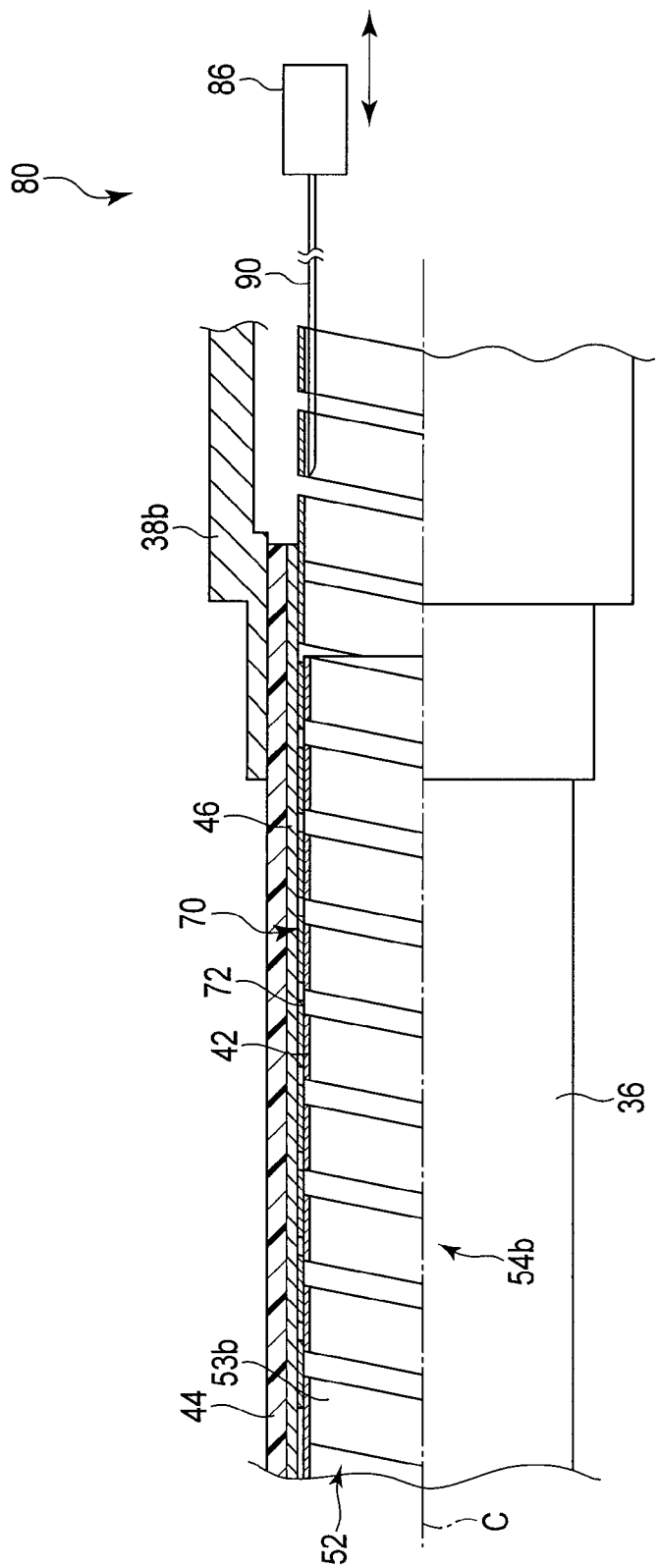
FIG. 7 is a schematic partial longitudinal sectional view showing the proximal end of the flexible tubular portion having the three-layer structure of the insertion portion, and a protection hood of an operation portion in the endoscope according to the first embodiment.
Figure 9B:
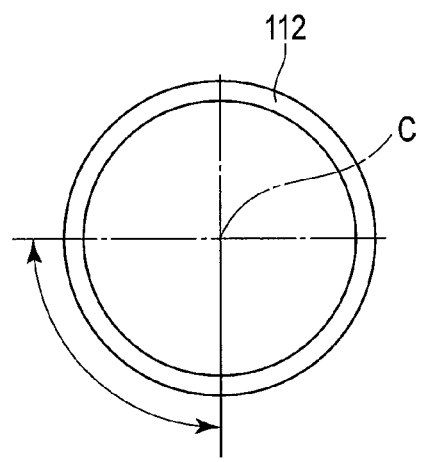
FIG. 9B is a schematic diagram showing a cylindrical rotor (knob) of the cam ring adjusting portion.
Figure 9C:
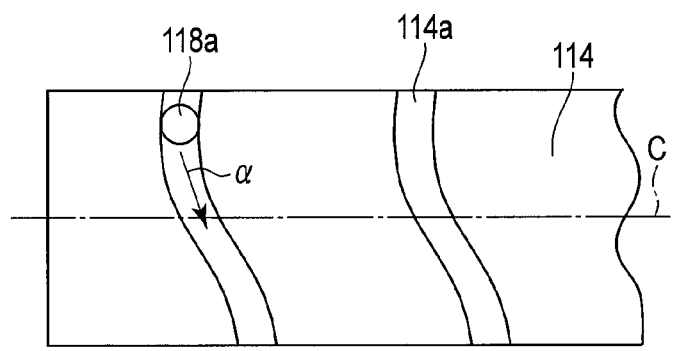
FIG. 9C is a schematic diagram showing a cam cylinder of the cam ring adjusting portion.
Figure 9D:
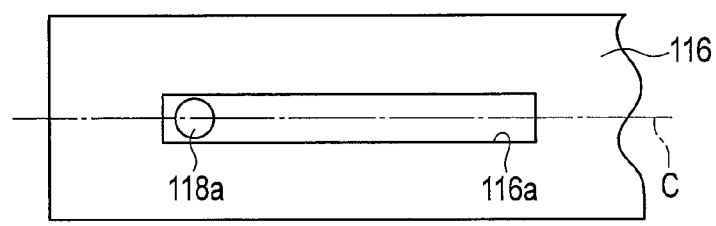
FIG. 9D is a schematic diagram showing a cylindrical tube of the cam ring adjusting portion.

As shown in FIG. 7, the inhibiting portion 70 includes a second helical tube 72 and a lever adjusting portion 80 that will be described later.

As shown in FIG. 7, in this embodiment, the second helical tube (inhibiting member) 72 movable in the axial direction of the spiral tube (hereinafter referred to as a first spiral tube when appropriate) 42 is located outside the sparsely wound portion 54b of the first spiral tube 42. The second helical tube 72 is preferably located between the first spiral tube 42 and the mesh tube 46.

The second helical tube 72 is formed in the same manner as, for example, the sparsely wound portion 54b of the first spiral tube 42. That is, the inside diameter of the second helical tube 72 is formed to be larger than the outside diameter of the sparsely wound portion 54b of the first spiral tube 42. Thus, the lever adjusting portion 80 is moved to diametrically stretch and contract the second helical tube 72 and thereby fasten the outer circumference of the sparsely wound portion 54b. This prevents the part of the sparsely wound portion 54b covered with the second spiral tube 72 from moving to the rear end side relative to the outer tube 44 and the mesh tube 46. Therefore, the part (movable range) of the proximal-side sparsely wound portion 54b of the first spiral tube 42 that can contract along the axial direction of the central axis C is a part from the distal end of the proximal-side sparsely wound portion 54b of the first spiral tube 42 to the distal end of the second helical tube 72, and is shorter than the overall length of the proximal-side sparsely wound portion 54b of the first spiral tube 42. Thus, the movable range is limited, and the movement of the sparsely wound portion 54b is inhibited to enhance the spring characteristics of the proximal-side sparsely wound portion 54b, and the whole flexible tubular portion 36 can be difficult to bend. When the length of the overlap between the sparsely wound portion 54b of the first spiral tube 42 and the second helical tube 72 is greater, a regulation length to regulate (inhibit) the movement of the sparsely wound portion 54b can be greater. Thus, when the length of the overlap between the sparsely wound portion 54b of the first spiral tube 42 and the second helical tube 72 is greater, the flexible tubular portion 36 can be more difficult to bend.

In the case described here, the winding directions of the first spiral tube 42 and the second helical tube 72 are opposite to each other. For example, the first spiral tube 42 is generally right-handed, and the second helical tube 72 is left-handed. That is, the winding direction of the linear member 42a of the first spiral tube 42 is opposite to the winding direction of a linear member 72a of the second spiral tube 72, so that it is possible to locate the linear members 42a of the first spiral tube 42 and the linear member 72a of the second helical tube 72 across each other when the second helical tube 72 is located on the outer circumference of the first spiral tube 42. Thus, when the outside second helical tube 72 is axially moved relative to the proximal-side sparsely wound portion 54b of the inside first spiral tube 42, it is possible to prevent the linear member 72a of the second spiral tube 72 from intervening between the linear members 42a of the proximal-side sparsely wound portion 54b of the first spiral tube 42. Thus, the second helical tube 72 can be more easily axially moved relative to the first spiral tube 42 than when the winding directions are the same.

As shown in FIG. 8A, the position of the distal end of the second helical tube 72 can be steplessly adjusted by the lever adjusting portion (inhibiting portion) 80.

The lever adjusting portion 80 has a lever 82 pivotally supported by the operation portion 14, a link member 84 having its proximal end coupled to the lever 82, a slider 86 coupled to the link member 84, a rail (guide portion) 88 which guides the slider 86 closer to or away from the distal end of the insertion portion 12, and a movable rod 90 coupled to the distal end of the link member 84.

The lever 82 can be rotated and steplessly moved between a position indicated by solid lines where a head portion 82a operated by the operator is exposed outside the operation portion 14, and a position indicated by broken lines. The link member 84 can move the slider 86 in a predetermined range along the rail 88 along the axial direction of the insertion portion 12 by the operation of the lever 82. The proximal end of the second helical tube 72 is fixed to the distal end of the movable rod 90. The movable rod 90 is movable to the distal side and the proximal side along the position parallel to the central axis C, and the second spiral tube 72 has the rigidity that permits free movement to the distal side and the proximal side along the central axis C.

Thus, the second helical tube 72 has a proximal end fixed to the movable rod 90, and a free distal end. The linear member 72a of the second helical tube 72 can diametrically stretch and contract along the central axis C. The edges of the linear members 72a come closer to each other when the linear members 72a of the second spiral tube 72 are moved to the distal side of the proximal-side sparsely wound portion 54b. The edges of the linear members 72a come away from each other when the linear members 72a are moved to the proximal side.

When the lever 82 is located at a solid line position in FIG. 8A, the proximal end of the second helical tube 72 is located in the vicinity of the main body 22 inside the protection hood 24 of the operation portion 14. When the lever 82 is located at a broken line position in FIG. 8A, the proximal end of the second spiral tube 72 is located in the vicinity of the proximal end of the insertion portion 12 inside the protection hood 24 of the operation portion 14 as compared to the situation in which the lever 82 is located at the solid line position.

It is also preferable that the winding directions of the first spiral tube 42 and the second spiral tube 72 are the same. In this case, the second spiral tube 72 can be rotated and thereby moved in the same axial direction as the first spiral tube 42.

Now, the function of the endoscope 10 having the flexible tubular portion 36 according to this embodiment is described.

The insertion portion 12 of the endoscope 10 is inserted into, for example, a twisting lumen from its distal end while the bending portion 34 is curved. At the same time, the flexible tubular portion 36 is deformed by the shape of the inside of the lumen under the external force F.

When the closely wound portion 52 of the flexible tubular portion 36 is bent in the lumen under the external force F which is equal to or more than the force that cancels the initial tension, the linear members 42a at the opposite position to which the external force F has been applied come away. Therefore, the sparsely wound portions 54a and 54b integrally formed with the closely wound portion 52 are deformed together. In this case, since the overall length of the spiral tube 42 is constant, the closely wound portion 52 can be bent so that the distance between the linear members 42a of the sparsely wound portions 54a and 54b is partly reduced.

The insertability into the lumen changes depending on the hardness of the flexible tubular portion 36 (the bending degree of the flexible tubular portion 36 when the external force F is applied thereto). That is, it is necessary in some cases that the hardness of the flexible tubular portion 36 be properly changed, for example, depending on the shape and softness of the lumen to be inserted into. The hardness of the flexible tubular portion 36 depends on the user's preference.

When the hardness of the flexible tubular portion 36 is adjusted, the head portion 82a of the lever 82 disposed in the operation portion 14 is moved in this embodiment.

If the head portion 82a of the lever 82 is pushed down toward the solid line position, the second spiral tube 72 is pulled toward the operation portion 14 by the movable rod 90. If the head portion 82a of the lever 82 is pushed down toward the broken line position, the second spiral tube 72 is pulled toward the distal side of the insertion portion 12 by the movable rod 90. Thus, when the head portion 82a of the lever 82 is located at the broken line position, the distal end of the second spiral tube 72 can be located closer to the proximal end of the bending portion 34 than when the head portion 82a is located at the solid line position. Therefore, the distal side of the sparsely wound portion 54b of the spiral tube 42 can be held by the second helical tube 72, so that it is possible to inhibit the movement relative to the outer tube 44 and the mesh tube 46 from the distal end to the proximal end of the held portion. Here, when the head portion 82a of the lever 82 is located at the broken line position, the movement of the sparsely wound portion 54b is regulated on the more distal side than when the head portion 82a is located at the solid line position, so that the distance from the proximal end of the closely wound portion 52 to the distal end of the regulated part (the distal end of the second spiral tube 72) is shorter. Consequently, the axial length of a buffering portion formed by the linear member 42a of the sparsely wound portion 54b is shorter, and the sparsely wound portion 54b is harder. That is, the flexible tubular portion 36 can be hard and strong as a whole, and becomes difficult to bend.

For example, when a force is applied from the outside of the outer tube 44 toward the central axis C, the movable range of the sparsely wound portions 54a and 54b is smaller. Therefore, more force to bring the linear members 42a into close contact with each other is applied to the closely wound portion 52 in addition to the initial tension than when the movement of the proximal side of the sparsely wound portion 54b is not inhibited by the second spiral tube 72. That is, the flexible tubular portion 36 allows not only the parts corresponding to the sparsely wound portions 54a and 54b but also the part corresponding to the closely wound portion 52 to be difficult to bend.

Since the second spiral tube 72 completely covers the outer circumferential surface of the proximal-side sparsely wound portion 54b of the first spiral tube 42 all round, a substantially equal force is applied in all the directions. It is therefore possible to prevent the first spiral tube 42 from varying in unbendability depending on its direction. That is, for example, the unbendability of the flexible tubular portion 36 in the U-direction can be substantially the same as the unbendability in the D-direction. The unbendability of the flexible tubular portion 36 not only in the U-direction and the D-direction but also in the L-direction and the R-direction can be substantially the same.

Therefore, when the flexible tubular portion 36 needs to be hard, that is, when the flexible tubular portion 36 needs to be strong, the lever 82 is pushed down toward the broken line position. On the other hand, when the flexible tubular portion 36 needs to be flexible, that is, when the flexible tubular portion 36 needs to be less strong, the lever 82 is pushed down toward the solid line position. The lever 82 can be stopped at a desired position between the solid line position and the broken line position. Thus, the second spiral tube 72 of the inhibiting portion 70 according to this embodiment allows the hardness of the flexible tubular portion 36 to be steplessly adjusted.

Although the movable rod 90 is moved by the operation force of the lever 82 via the link member 84 and the slider 86 in the example described according to this embodiment, it is also preferable to gear, for example, an unshown linear motor with the lever 82 to form a similar mechanism (the lever adjusting portion 80).

As described above, the following advantageous effects can be obtained according to this embodiment.

Since the length of the outer layer (the outer tube 44 and the mesh tube 46) does not change when the spiral tube 42 is bent, a constant overall length of the spiral tube 42 is maintained by the increase and decrease of the distance between the linear members 42a of the spiral tube 42 in the direction along the central axis C. The inhibiting portion 70 which inhibits the movement of the sparsely wound portion 54b relative to the outer layer has the second spiral tube 72. The second spiral tube 72 functions so that the range in which the linear members 42a can be brought closer and brought away in the direction along the central axis C is smaller than when the movement between the linear members 42a is not inhibited in the sparsely wound portion 54b. That is, this is equal to or close to the reduction of the length of the spiral tube 42. It is therefore possible to change the spring characteristics of the spiral tube 42 by the second spiral tube 72, and also adjust the flexible tubular portion 36 (adjust the hardness of the flexible tubular portion 36) so that the flexible tubular portion 36 will be hard and thus strong and difficult to bend or will be flexible and thus less strong and easy to bend.

When the second spiral tube 72 is used, the sparsely wound portion 54b of the spiral tube 42 can be covered all round because the second spiral tube 72 is cylindrically formed. Therefore, the flexible tubular portion 36 can have a constant flexibility regardless of its bending direction even when the flexible tubular portion 36 needs to be hard or flexible. In other words, the movement of the spiral tube 42 on the distal side is not inhibited (restricted) as compared to the position where the movement of the spiral tube 42 is inhibited, so that there is no anisotropy in the circumferential direction, and the same flexibility and isotropy are also provided in different directions.

The second spiral tube 72 having the continuous linear member 72a is moved relative to the spiral tube 42 in the direction along the central axis C. Thus, for example, when the second spiral tube 72 is moved forward or backward, the flexibility can be steplessly adjusted in accordance with the position where the second spiral tube 72 is moved.

Furthermore, the second spiral tube 72 is only moved relative to the spiral tube 42 in the axial direction, and it is unnecessary to apply force or remove this force, for example, as in the above-mentioned spiral tube according to Jpn. Pat. Appln. KOKAI Publication No. 2003-19109. Therefore, the second spiral tube 72 can be less frequently exchanged. That is, the insertion portion 12 including the flexible tubular portion 36 can be less frequently disassembled and maintained.

[First Modification]

Now, a first modification of the first embodiment is described with reference to FIG. 9A to FIG. 9D. Although the lever adjusting portion 80 of the inhibiting portion 70 is used to move the second spiral tube 72 in the example described according to the first embodiment, a cam ring adjusting portion 110, for example, may be used as shown in FIG. 9A to FIG. 9D.

As shown in FIG. 9A to FIG. 9D, the cam ring adjusting portion 110 includes a cylindrical rotor (knob) 112 rotatable relative to the operation portion 14 around the central axis C of the insertion portion 12, a cam cylinder 114 provided inside the cylindrical rotor 112, a cylindrical tube 116 provided inside the cam cylinder 114, and a movable ring (slider) 118 provided inside the cylindrical tube 116.

The cylindrical rotor 112 and the cam cylinder 114 are fixed by, for example, screws. In the cam cylinder 114, a cam groove 114a is spirally formed around the central axis C. The cylindrical tube 116 is fixed to at least one of the main body 22 and the protection hood 24 of the operation portion 14. A long hole 116a having a longitudinal direction parallel to the central axis C is formed in the cylindrical tube 116. A movable pin 118a disposed in the long hole 116a of the cylindrical tube 116 and the cam groove 114a of the cam cylinder 114 is fixed to the movable ring 118.

The cylindrical rotor 112 and the cam cylinder 114 rotate around the central axis C at their positions. In this case, depending on the rotation directions of the cylindrical rotor 112 and the cam cylinder 114, the cam cylinder 114 moves the movable pin 118a through the cam groove 114a relative to the cam cylinder 114, for example, as indicated by the arrow α.

Since the movable pin 118a also passes through the long hole 116a of the cylindrical tube 116, the movable ring 118 moves parallel to the central axis C together with the movable pin 118a closer to and away from the distal end of the insertion portion 12 along the long hole 116a. That is, the movable ring 118 can be moved parallel to the direction of the central axis C if the cylindrical rotor 112 is rotated around the central axis C.

If the cylindrical rotor 112 is rotated, the movable pin 118a moves as indicated by the arrow β. The movable range of the movable ring 118 is determined by the shape of the cam groove 114a of the cam cylinder 114 and by the axial length of the long hole 116a of the cylinder 116 parallel to the central axis C.

The proximal end of the movable rod 90 formed in a similar manner as the above-mentioned lever adjusting portion (inhibiting portion) 80 is fixed to the movable ring 118. Thus, the second helical tube 72 fixed to the distal end of the movable rod 90 can be moved along the central axis C. Therefore, when the cam ring adjusting portion 110 is used, it is also possible to move the second helical tube 72 relative to the outer tube 44 and properly inhibit the movement of the proximal-side sparsely wound portion 54b of the spiral tube 42, as in the case where the lever adjusting portion 80 is used.

The lever adjusting portion 80 and the cam ring adjusting portion 110 in the example described according to the first embodiment moves the second helical tube 72 without rotating. However, it is also preferable to use a known mechanism to move the second spiral tube 72 closer to and away from the distal end of the insertion portion 12 while rotating the second spiral tube 72 around the central axis C.

Although the second helical tube 72 is moved straight in the example described according to this modification, it is also preferable to move the second spiral tube in the direction along the central axis C while rotating the second spiral tube without using the cylinder 116. This is particularly preferable when the winding directions of the first spiral tube 42 and the second helical tube 72 are the same.

[Second Modification]

Now, a second modification of the first embodiment is described with reference to FIG. 10A. Although the inhibiting portion 70 uses the second helical tube 72 in the example described according to the first embodiment including the first modification, an example described below may be used.

Figure 10A:
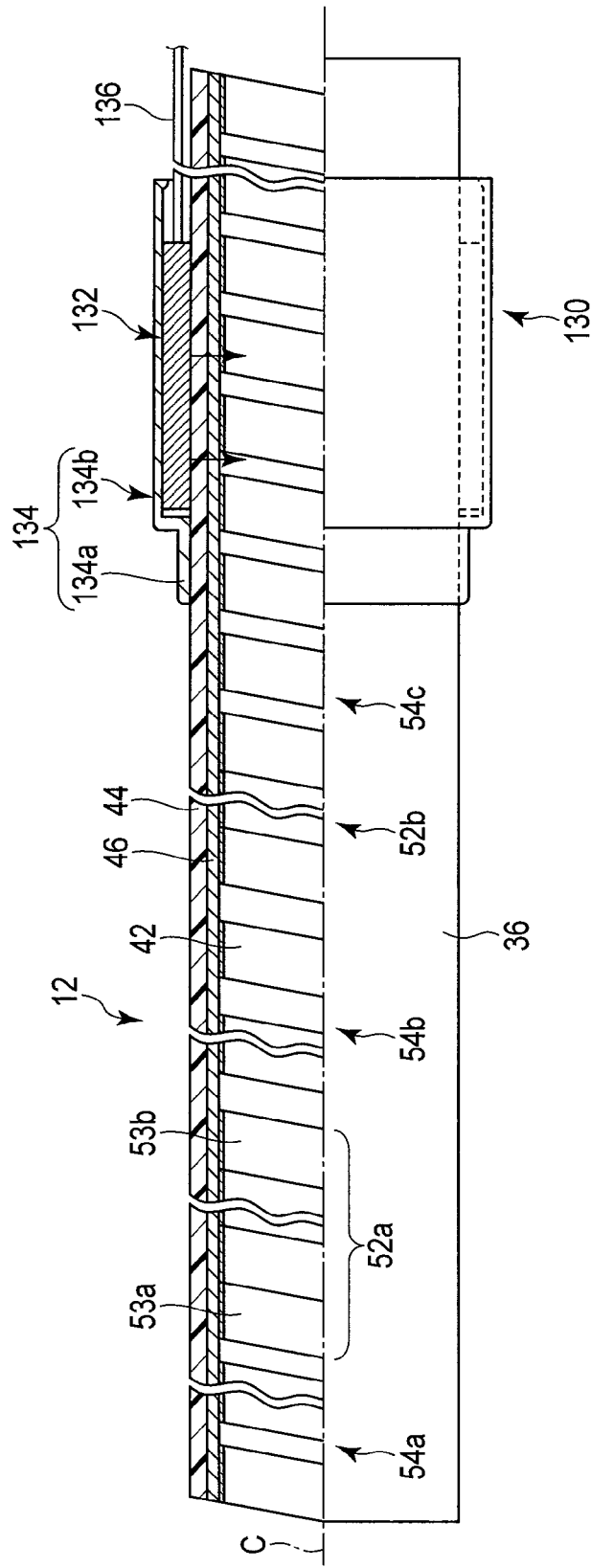
FIG. 10A is a schematic partial longitudinal sectional view showing a balloon mechanism provided in the flexible tubular portion of the insertion portion in an endoscope according to a second modification of the first embodiment.

As shown in FIG. 10A, a balloon mechanism (inhibiting portion) 130 movable to the distal side and the proximal side along the central axis C is provided on the outer circumference of the flexible tubular portion 36.

The balloon mechanism (inhibiting portion) 130 has an inflatable (expandable) and deflatable annular balloon (inhibiting member) 132, and a regulating member 134 which is provided outside the balloon 132 and which prevents the balloon 132 spreading outward. The regulating member 134 is cylindrically formed. The regulating member 134 has an annular sliding portion 134a having an inside diameter slightly larger than the outer tube 44 of the flexible tubular portion 36, and a cylindrical balloon receiving portion 134b which is provided integrally with the proximal side of the sliding portion 134a and which allows the balloon 132 to be disposed between the balloon receiving portion 134b and the outer tube 44. The proximal end of the balloon receiving portion 134b is formed to pass a tube 136 for letting air in and out of the balloon 132 and to allow the balloon 132 to be let in and out while the regulating member 134 is disposed outside the flexible tubular portion 36. An unshown pump is connected to the tube 136.

The regulating member 134 of the balloon mechanism 130 is moved relative to the outside of the outer tube 44 located at the position corresponding to the proximal-side sparsely wound portion 54b to locate the balloon mechanism 130 at a proper position. Air is let into the balloon 132 via the tube 136 in this state to inflate the balloon 132. In this case, the diametrically outward inflation of the balloon 132 is regulated by the balloon receiving portion 134b of the regulating member 134. Thus, the balloon 132 circumferentially presses the outer tube 44, the mesh tube 46, and the proximal-side sparsely wound portion 54b of the spiral tube 42 toward the central axis C. Here, unshown inner objects such as a light guide, an imaging cable, and various tubes are provided inside the insertion portion 12. Thus, the proximal-side sparsely wound portion 54b is held between the outer tube 44 and the mesh tube 46 that are pressed by the balloon 132, and the inner objects. Therefore, it is possible to inhibit the movement of the proximal-side sparsely wound portion 54b relative to the outer layer (the outer tube 44 and the mesh tube 46).

Since the balloon mechanism 130 is movable on the outer circumferential surface of the flexible tubular portion 36 along the longitudinal direction of the central axis C, it is possible to easily inhibit the movement of the sparsely wound portion 54b at a proper position relative to the outer layer. The balloon mechanism 130 is located outside the flexible tubular portion 36, so that there is no influence on the inside of the flexible tubular portion 36, and the insertion portion 12 can be less frequently maintained.

According to this modification, the above-mentioned second helical tube 72 can be used at the same time in addition to the balloon 132.

[Third Modification]

Now, a third modification of the first embodiment is described with reference to FIG. 10B.

Figure 10B:
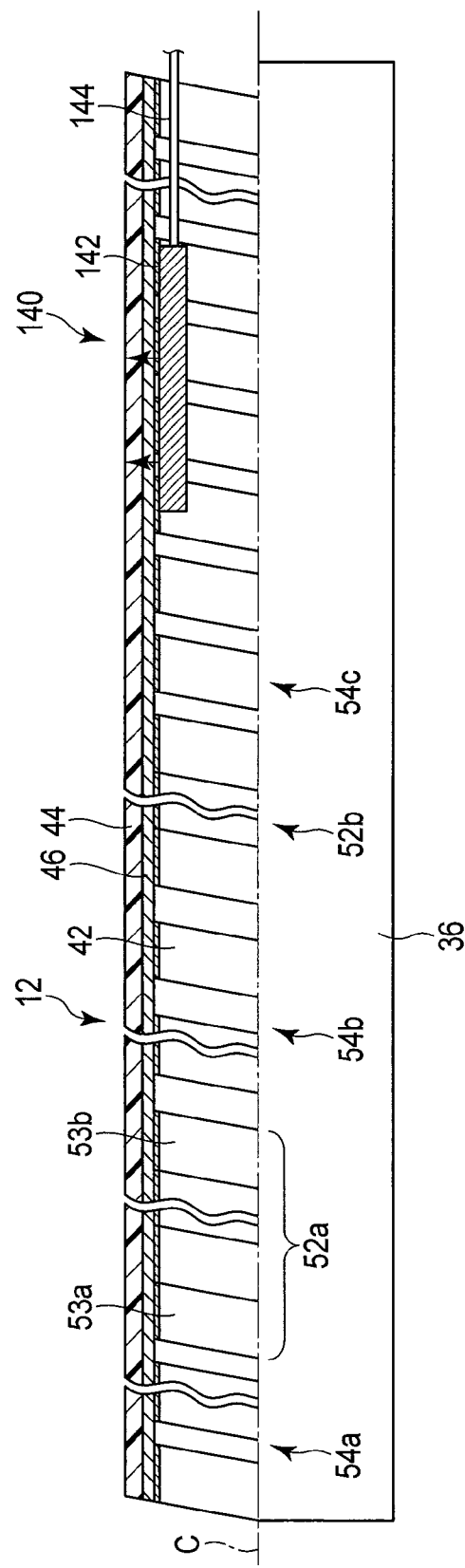
FIG. 10B is a schematic partial longitudinal sectional view showing a balloon mechanism provided inside the flexible tubular portion of the insertion portion in an endoscope according to a third modification of the first embodiment.

As shown in FIG. 10B, a balloon mechanism (inhibiting portion) 140 movable to the distal side and the proximal side along the central axis C is provided on the inner circumference of the spiral tube 42 of the flexible tubular portion 36. The balloon mechanism (inhibiting portion) 140 has an inflatable (expandable) and deflatable balloon (inhibiting member) 142, and a tube 144 for letting air in and out the balloon 142. The balloon 142 may be annular, or may be formed to inflate into, for example, an elliptic shape. In the case described here, the balloon 142 mainly inflates into the elliptic shape.

The balloon 142 according to this modification can move along the central axis C relative to the inside of the proximal-side sparsely wound portion 54b of the spiral tube 42 by using, for example, the lever adjusting portion 80 (see FIG. 8A and FIG. 8B) described in the first embodiment and the cam ring adjusting portion 110 (see FIG. 9A) in the first modification.

Thus, when the hardness of the flexible tubular portion 36 is changed, the lever adjusting portion 80 (see FIG. 8A and FIG. 8B) described in the first embodiment and the cam ring adjusting portion 110 (see FIG. 9A) in the first modification, for example, are used to locate the balloon mechanism 140 at a proper position along the central axis C relative to the flexible tubular portion 36. In this state, the balloon 142 of the balloon mechanism 140 is inflated. In this case, the balloon 142 inflates to press the inner circumference of the sparsely wound portion 54b outwardly (the mesh tube 46 and the outer tube 44), and also inflates toward the central axis C. In this case, the inflation of the balloon 142 is regulated by the inner objects (e.g., a light guide bundle and an observation cable). Thus, no regulating member to regulate the inflation toward the central axis C is needed inside the balloon 142. When the balloon 142 is inflated in this way, the proximal-side sparsely wound portion 54b of the spiral tube 42 can be held between the mesh tube 46 and the outer tube 44. Therefore, it is possible to inhibit the movement of the sparsely wound portion 54b relative to the outer tube 44.

When the balloon 142 is formed to inflate into the elliptic shape, the movement of the spiral tube 42 closer to the distal side than the position where the balloon 142 is inflated and the movement of the spiral tube 42 is inhibited is not inhibited (not restricted). Thus, there is no anisotropy in the circumferential direction on the distal side from the position where the movement of the spiral tube 42 is inhibited by the balloon 142, and the flexibility is the same even in different directions, and the bending strength can be isotropic.

[Fourth Modification]

Now, a fourth modification of the first embodiment is described with reference to FIG. 11. As shown in FIG. 11, a catching portion 150 movable along the central axis C of the flexible tubular portion 36 is provided as an inhibiting portion on the outer circumference of the flexible tubular portion 36.

For example, a collet chuck or a pin vice is preferably used as the catching portion 150. In the example described here, the collet chuck is used.

The chucking portion (inhibiting portion) 150 has a press member (collet) 152 which is divided into parts and which is substantially annular as a whole, and an annular holder (nut) 154 provided outside the press member 152. The holder 154 holds the press member 152 divided into parts.

Threaded portions that can be screwed to each other are formed on the outer circumferential surface of the divided press member 152 and on the inner circumferential surface of the holder 154. The outer circumferential surface of the press member 152 and the outer circumferential surface of the holder 154 respectively have tapered surfaces 152a and 154a so that the inside diameter of the press member 152 is reduced in accordance with the fastening of the holder 154 to the press member 152.

Thus, when the outside of the flexible tubular portion 36 is moved along the central axis C, the holder 154 is loosened relative to the press member 152. When the outside of the flexible tubular portion 36 is pressed toward the central axis C, the holder 154 is fastened to the press member 152. In this case, the press member 152 circumferentially presses the outer tube 44, the mesh tube 46, and the proximal-side sparsely wound portion 54b of the spiral tube 42 toward the central axis C. Here, unshown inner objects such as a light guide, an imaging cable, and various tubes are provided inside the insertion portion 12. Thus, the proximal-side sparsely wound portion 54b is held between the outer tube 44 and the mesh tube 46 that are pressed by the press member 152, and the inner objects. Therefore, it is possible to inhibit the movement of the proximal-side sparsely wound portion 54b relative to the outer tube 44.

Since the catching portion 150 is movable on the outer circumferential surface of the flexible tubular portion 36 along the longitudinal direction of the central axis C, it is possible to easily inhibit the movement of the sparsely wound portion 54b at a proper position relative to the outer layer.

Since the chucking portion 150 is only moved relative to the outer tube 44, the components to apply the external force to change the hardness of the flexible tubular portion 36 are located outside the operation portion 14. Therefore, the components inside the flexible tubular portion 36 can be less frequently exchanged.

[Fifth Modification]

Now, a fifth modification of the first embodiment is described with reference to FIG. 12A and FIG. 12B.

As shown in FIG. 12A, an actuator mechanism 160 is provided as an inhibiting portion inside the proximal-side sparsely wound portion 54b of the spiral tube 42 of the flexible tubular portion 36.

The actuator mechanism (inhibiting portion) 160 has a piezoelectric element (inhibiting member) 162 as an actuator, and a power supply 164 for driving the piezoelectric element 162. The piezoelectric element 162 is supported on the inner circumferential surface of the sparsely wound portion 54b of the spiral tube 42 of the flexible tubular portion 36. In this case, the piezoelectric element 162 is located to face at least two linear members 42a of the sparsely wound portion 54b. Electric energy is applied to the piezoelectric element 162 from the power supply 164, and the piezoelectric element 162 thereby presses the inner circumferential surfaces of at least two linear members 42a of the sparsely wound portion 54b at the same time. Thus, the movement of the linear members 42a can be regulated.

There may be one or more piezoelectric elements 162.

When only one piezoelectric element 162 is used, for example, the piezoelectric element 162 is preferably formed movably along the inner circumferential surface of the sparsely wound portion 54b of the spiral tube 42. For example, the above-mentioned lever adjusting portion 80 or cam ring adjusting portion 110 can be used as the structure to move the piezoelectric element 162. Therefore, the hardness of the flexible tubular portion 36 can be adjusted by driving the piezoelectric element 162 at a proper position.

More than one piezoelectric element 162 may be provided at proper intervals on the inner circumferential surface of the sparsely wound portion 54b of the spiral tube 42. In this case, the hardness of the flexible tubular portion 36 can be adjusted by driving a selected piezoelectric element 162. That is, those of the actuators that should be driven are preferably set to be drivable.

As shown in FIG. 12B, a rubber artificial muscle 166 can be used as the actuator instead of the piezoelectric element 162. This artificial muscle 166 can be used in a manner similar to the piezoelectric element 162. The flexible tubular portion 36 may be locally hard in part because the piezoelectric element 162 is made of a hard material. However, the artificial muscle 166 is made of the rubber material, and can therefore prevent the flexible tubular portion 36 from being locally hard in part.

According to this modification, the whole inner circumferential surface of the proximal-side sparsely wound portion 54b of the spiral tube 42 is not diametrically outwardly pressed relative to the central axis C. For example, at least two linear members 42a of the sparsely wound portion 54b are locally pressed by the piezoelectric element 162. Thus, by only pressing at least two linear members 42a, it is possible to inhibit the movement of the part of the proximal-side sparsely wound portion 54b of the spiral tube 42 closer to the proximal side than the pressed position relative to the outer layer (the mesh tube 46 and the outer tube 44). On the side closer to the distal side than the pressed position of the piezoelectric element 162, there is nothing to inhibit the movement of the linear member 42a of the sparsely wound portion 54b. Therefore, the flexibility of the flexible tubular portion 36 can also be substantially uniform in the circumferential direction if an actuator such as the piezoelectric element 162 or the artificial muscle 166 is locally arranged.

When, for example, the piezoelectric element 162 and the artificial muscle 166 are used as the actuators, the inside of the flexible tubular portion 36 can be less frequently maintained.

[Fifth Modification]

Now, a sixth modification of the first embodiment is described with reference to FIG. 13A and FIG. 13B. As shown in FIG. 13A and in FIG. 13B which is a sectional view taken along the line 13B-13B in FIG. 13A, a C-ring fastening mechanism 170 is provided as an inhibiting portion outside the proximal-side sparsely wound portion 54b of the spiral tube 42 of the flexible tubular portion 36.

The C-ring fastening mechanism (inhibiting portion) 170 includes a C-ring 172 and a C-ring receiving portion 174. The C-ring 172 has a ring-shaped portion 182, and a pair of protrusions 184 which are bent from the ring-shaped portion 182 toward the inner circumferential side. The pair of protrusions 184 protrude, for example, toward the distal side of the insertion portion 12, and have elasticity to come closer to or away from each other. The C-ring receiving portion 174 has a tapered surface 192 which brings the pair of protrusions 184 of the C-ring 172 closer to each other.

The C-ring 172 and the C-ring receiving portion 174 can be moved along the axial direction by the above-mentioned lever adjusting portion 80 or cam ring adjusting portion 110. If the pair of protrusions 184 of the C-ring 172 are put into the tapered surface 192 of the C-ring receiving portion 174, the inside diameter of the ring-shaped portion 182 coupled to the pair of protrusions 184 is reduced as the pair of protrusions 184 of the C-ring 172 come closer to each other. Thus, the ring-shaped portion 182 of the C-ring 172 presses the outer circumferential surface of the sparsely wound portion 54b toward the central axis C, and the movement of the sparsely wound portion 54b can be inhibited.

Second Embodiment

Now, a second embodiment is described with reference to FIG. 14A and FIG. 14B. This embodiment is a modification of the first embodiment, and like reference numerals denote members equal to those in the members explained in the first embodiment, thereby omitting a detailed explanation thereof. It should be understood that the examples described in the first embodiment including its modifications can be combined with the examples described in this embodiment (including its modifications described below). That is, for example, the second spiral tube 72 described in the first embodiment can be applied to this embodiment. The same also applies to a third embodiment described later.

In the example described according to this embodiment, the user of the endoscope 10 presses, as an inhibiting portion, the outer surface of the outer tube 44 and thereby inhibits the movement of the proximal-side sparsely wound portion 54b of the spiral tube 42 relative to the outer tube 44. By way of example, at least one depression (thin portion) is formed in the outer surface of the outer tube 44 which is the outer surface of the flexible tubular portion 36 in the example described here. The user of the endoscope 10 presses this depression, and it is thereby possible to easily inhibit the movement of the proximal-side sparsely wound portion 54b of the spiral tube 42 relative to the outer tube 44.

Figure 14B:
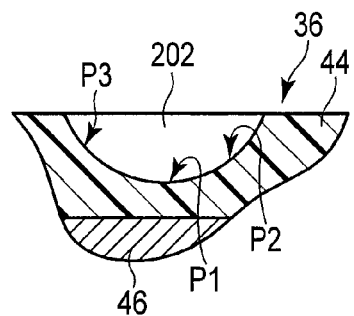
FIG. 14B is a schematic cross sectional view taken along the line 14B-14B in FIG. 14A.

As shown in FIG. 14A, in this embodiment, the surface of the outer tube 44 has an inhibiting portion 200. The inhibiting portion 200 has multiple (here, three) depressions 202, 204, and 206 on the surface of the outer tube 44. The depressions 202, 204, and 206 are formed into substantially circular shapes similar in diameter. As shown in FIG. 14B which is a sectional view taken along the line 14B-14B in FIG. 14A, each of the depressions 202, 204, and 206 is formed to be thinnest in its center and deep in the surface of the outer tube 44, and becomes thicker and shallower in the surface of the outer tube 44 in parts closer to the edge. Thus, when the outer tube (outer layer) 44 is pressed toward the central axis C, the mesh tube 46 and the spiral tube 42 can be more easily moved because of the presence of the depressions 202, 204, and 206 where the thickness of the outer tube 44 is reduced than when the position of the outer tube 44 off the depressions is pressed toward the central axis C. Consequently, the movement of the spiral tube 42 can be effectively inhibited.

The depressions 202, 204, and 206 are formed on the line parallel to the central axis C, for example, at appropriate intervals D. The most distal depression 202 is preferably formed so that its distal end is located closer to the proximal side, for example, about 200 mm to several hundred mm from the distal end (end coupled to the bending portion 34) of the outer tube 44 of the flexible tubular portion 36.

Thus, if the user of the endoscope 10 presses one of the three depressions 202, 204, and 206 of the outer tube 44 while holding the flexible tubular portion 36, for example, with the thumb, the proximal-side sparsely wound portion 54b of the spiral tube 42 is moved toward the central axis C through the outer tube 44 and the mesh tube 46. In this case, the inner circumferential surface of the sparsely wound portion 54b abuts on inner objects, so that the movement of the sparsely wound portion 54b relative to the outer layer (the outer tube 44 and the mesh tube 46) is inhibited.

As a result, when one of the depressions 202, 204, and 206 is pressed, the flexible tubular portion 36 can be more unbendable and lower in flexibility due to the function similar to that described in the first embodiment than before one of the three depressions 202, 204, and 206 is pressed. That is, when one of the depressions 202, 204, and 206 is pressed, the flexible tubular portion 36 can be stronger and harder.

As has been described in, for example, the third modification (see FIG. 10B) and the fifth modification (see FIGS. 12A and 12B) of the first embodiment, it is unnecessary to press the whole outer circumference of the outer tube 44 of the flexible tubular portion 36 in this embodiment. That is, by only pressing a part (one of the depressions 202, 204, and 206) of the outer circumference of the outer tube 44, it is possible to adjust the degree of inhibiting the movement of the sparsely wound portion 54b closer to the distal side than the pressed position relative to the outer tube 44, and adjust the hardness of the flexible tubular portion 36.

The depressions 202, 204, and 206 can be used as marks of positions to be pressed by the user of the endoscope 10 with a finger (positions that are easily pressed). Similar functions can also be obtained if the user of the endoscope 10 presses parts of the outer tube 44 other than the depressions 202, 204, and 206. However, it can be easily imagined that more force is required to adjust the degree of inhibiting the movement of the sparsely wound portion 54b relative to the outer tube 44 than when the depressions 202, 204, and 206 are used.

Here, among the three depressions 202, 204, and 206, the depression 202 is located closer to the distal side of the flexible tubular portion 36 than the depressions 204 and 206. Thus, for example, when the center of the depression 202 is pressed, the movement of the sparsely wound portion 54b can be inhibited at a position closer to the distal end of the flexible tubular portion 36 than when the centers of the depressions 204 and 206 are pressed. As has been described above in the example in which the second spiral tube 72 (see FIG. 7) is used, the flexible tubular portion 36 can be stronger and harder if the length between the distal end of the sparsely wound portion 54b and the position where the movement relative to the outer layer (the outer tube 44 and the mesh tube 46) is inhibited is smaller. Therefore, the degree of inhibiting the movement of the sparsely wound portion 54b relative to the outer tube 44 can be higher when the depression 202 on the distal side of the flexible tubular portion 36 is pressed than when one of the depressions 204 and 206 on the proximal side of the depression 202 is pressed. Thus, the degree of inhibiting the movement of the sparsely wound portion 54b relative to the outer tube 44 can be changed by which of the depressions 202, 204, and 206 is to be pressed. It is appreciated that the degree of inhibiting the movement of the sparsely wound portion 54b is changed by the degree of force to press the depressions 202, 204, and 206.

The depressions 202, 204, and 206 are located on the surface of the outer tube 44, so that when changing from the pressing of the distal-side depression 202 to the pressing of the proximal-side depression 206, the user of the endoscope 10 only slides the right hand holding the flexible tubular portion 36 along the axial direction of the flexible tubular portion 36. Thus, the user of the endoscope 10 can adjust the hardness of the flexible tubular portion 36 without taking the hand off the flexible tubular portion 36.

As shown in FIG. 14B, the longitudinal section through the depression 202 is thin in the center and thicker closer to the edge. Thus, if the same force is applied to positions indicated by the signs P1 and P2 in FIG. 14B toward the central axis C, the deformation amount of the proximal-side sparsely wound portion 54b of the spiral tube 42 can be greater when the position indicated by the sign P1 is pressed than when the position indicated by the sign P2 is pressed. Therefore, even the same depression 202 can more effectively inhibit the movement of the sparsely wound portion 54b when the position indicated by the sign P1 is pressed than when the position indicated by the sign P2 is pressed. That is, the flexibility of the flexible tubular portion 36 can be adjusted by properly changing the position to press even in the same depression 202.

The position indicated by the sign P2 and the position indicated by the sign P3 in FIG. 14B show positions substantially at the same height from the rear surface of the outer tube 44. In this case, the position indicated by the sign P3 is closer to the distal side of the flexible tubular portion 36 than the position indicated by the sign P2. Therefore, the hardness (strength) of the flexible tubular portion 36 can be adjusted by changing the pressing position in the depression 202 not only in the height direction but also in the axial direction of the central axis C. Thus, the flexibility of the flexible tubular portion 36 can be adjusted not only by selecting the depressions 202, 204, and 206 but also by properly changing the position to press in one depression 202.

In particular, when the pressing position is properly changed in one depression 202, the user of the endoscope 10 can adjust the hardness of the flexible tubular portion 36 without taking the hand off the flexible tubular portion 36 while hardly moving the right hand holding the flexible tubular portion 36.

In the inhibiting portion 200 according to this embodiment, the depressions 202, 204, and 206 are only formed, and no particular maintenance of the flexible tubular portion 36 is therefore needed.

[First Modification]

Now, a first modification of the second embodiment is described with reference to FIG. 14C and FIG. 14D.

Figure 14C:
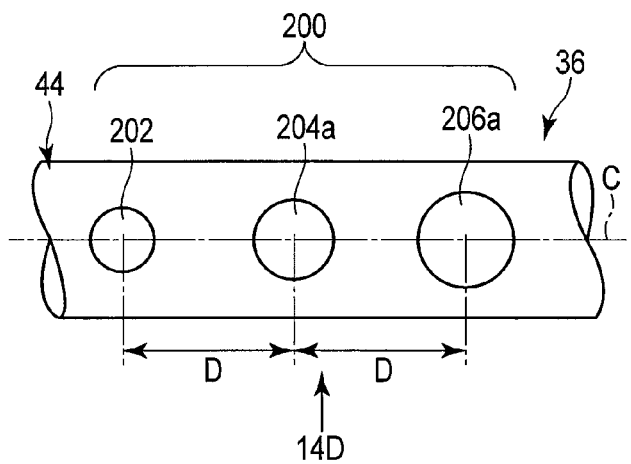
FIG. 14C is a schematic front view showing the outer circumferential surface of the flexible tubular portion in the insertion portion of the endoscope according to a first modification of the second embodiment.
Figure 14D:
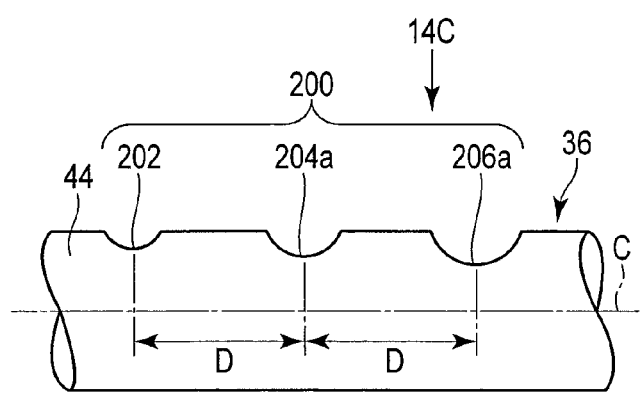
FIG. 14D is a schematic side view showing the outer circumferential surface of the flexible tubular portion in the insertion portion of the endoscope according to the first modification of the second embodiment.

As shown in FIG. 14C and FIG. 14D, the inhibiting portion 200 has multiple (here, three) depressions 202, 204a, and 206a on the surface of the outer tube 44. The depressions 202, 204a, and 206a are formed into substantially circular shapes different in diameter. Here, the depressions 202, 204a, and 206a are arranged in such an order that the diameter is smaller on the distal side and larger on the proximal side. Although not shown in detail, the depressions 202, 204a, and 206a have the same thickness in the depth direction. That is, the depth in the center of the depressions 202, 204a, and 206a is constant.

In this case, the depressions 202, 204a, and 206a are different in diameter, so that the area in which the outer tube 44 moves toward the central axis C tends to be larger when the depressions 204a and 206a are pressed than when the depression 202 is pressed. Therefore, the movement of the sparsely wound portion 54b relative to the outer layer (the outer tube 44 and the mesh tube 46) can be inhibited in a wider range by the depressions larger in area (the proximal-side depressions 204a and 206a rather than the depression 202).

Thus, it is possible to adjust the degree of inhibiting the movement of the sparsely wound portion 54b closer to the distal side than the position where the depressions 202, 204a, and 206a of the outer tube 44 are pressed relative to the outer layer.

[Second Modification]

Now, a second modification of the second embodiment is described with reference to FIG. 15A.

Figure 15A:
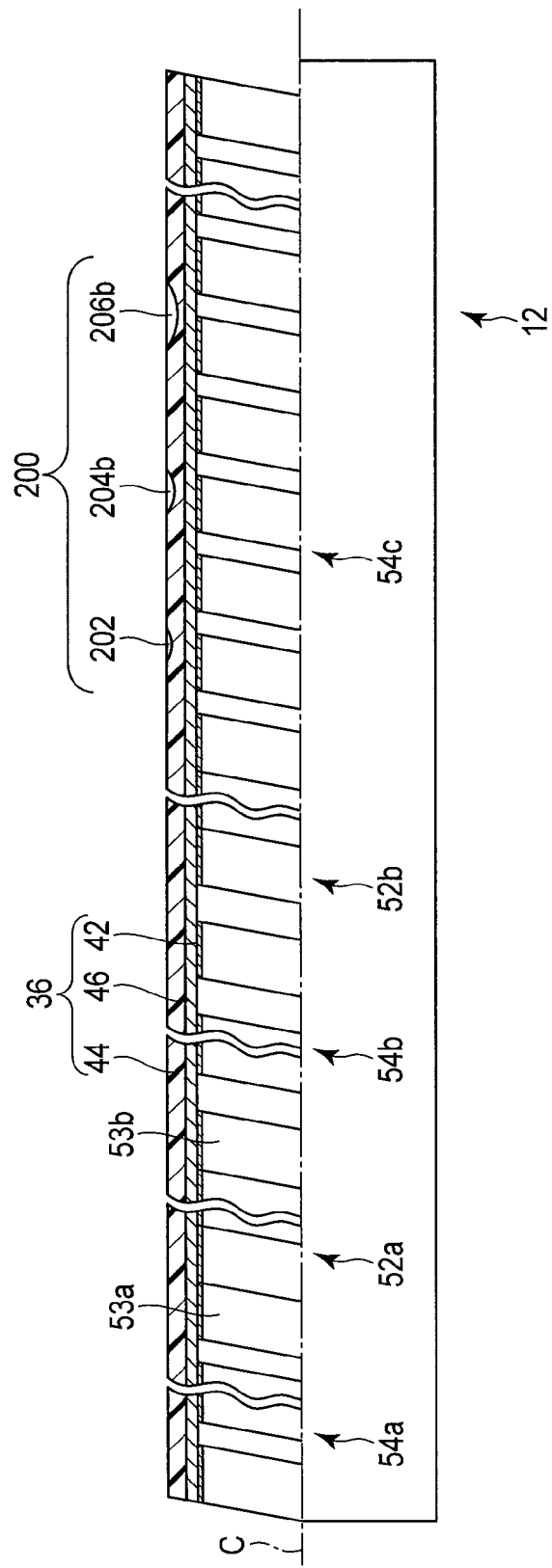
FIG. 15A is a schematic partial longitudinal sectional view showing depressions provided at proper intervals along a direction parallel to the central axis in the flexible tubular portion of the insertion portion in the endoscope according to a second modification of the second embodiment.

As shown in FIG. 15A, the shape of the depressions of the inhibiting portion 200 shown in FIG. 14A to FIG. 14D can be suitably changed. The spiral tube 42 described in the example according to this modification has two closely wound portions 52a and 52b, and three sparsely wound portions 54a, 54b, and 54c.

As shown in FIG. 15A, the inhibiting portion 200 has multiple (here, three) depressions 202, 204b, and 206b on the surface of the outer tube 44. The depressions 202, 204b, and 206b are formed into substantially circular shapes different in diameter, and are different in depth. Here, the depth in the surface of the outer tube 44 increases in the order of the distal-side depression 202, the depression 204b on the proximal side of the depression 202, and the depression 206b on the proximal side of the depression 204b. The depressions 202, 204b, and 206b are thinnest in their centers. That is, the thickness is small in the centers of the depressions 204b and 206b closer to the proximal side than the depression 202 as compared with the thickness in the thinnest center of the depression 202.

In this case, when the depressions 204b and 206b closer to the proximal side than the depression 202 are pressed, the area in which the outer tube 44 moves toward the central axis C tends to be larger if the same press force is applied to the centers of these depressions. Therefore, the movement of the sparsely wound portion 54c relative to the outer layer can be inhibited in a wider range by the depressions larger in area (the proximal-side depressions 204b and 206b rather than the depression 202).

Thus, it is possible to adjust the degree of inhibiting the movement of the sparsely wound portion 54c closer to the distal side than the position where the depressions 202, 204b, and 206b of the outer tube 44 are pressed relative to the outer layer.

[Third Modification]

Now, a third modification of the second embodiment is described with reference to FIG. 15B. Here, the second modification shown in FIG. 15A is used to describe the third modification.

As shown in FIG. 15B, for example, a press member (inhibiting portion) 210 formed by a C-ring can be used for the depressions 202, 204b, and 206b. The inside diameter of this press member 210 is slightly larger than the outside diameter of the flexible tubular portion 36, and the press member 210 is movable along the central axis C of the flexible tubular portion 36. For example, the C-ring-shaped press member 210 has, at one of its two ends, a projection 212 protruding toward the central axis C.

For example, when the depression 204b is pressed as shown in FIG. 15B, the ends are brought closer so that the diameter of the press member 210 is reduced. As a result, the projection 212 moves toward the central axis C, and the depression 204b can be pressed. Thus, the movement of the sparsely wound portion 54c relative to the outer tube 44 can be inhibited.

The press member 210 can also be used for the above-mentioned depressions shown in FIG. 14A to FIG. 14D. The press member 210 can also be used for the outer tube 44 having no depression shown in FIG. 16A to FIG. 19B described later, or for positions out of the depressions.

[Fourth Modification]

Now, a fourth modification of the second embodiment is described with reference to FIG. 16A to FIG. 16D.

The shapes of the depressions in the inhibiting portion 200 shown in FIG. 14A to FIG. 14D can be suitably changed as shown in FIG. 16A to FIG. 16D. The depressions shown in FIG. 16A to FIG. 16D are preferably formed so that their distal ends are located closer to the proximal side, for example, about 200 mm to several hundred mm from the distal end (end coupled to the bending portion 34) of the outer tube 44 of the flexible tubular portion 36.

Figure 16A:
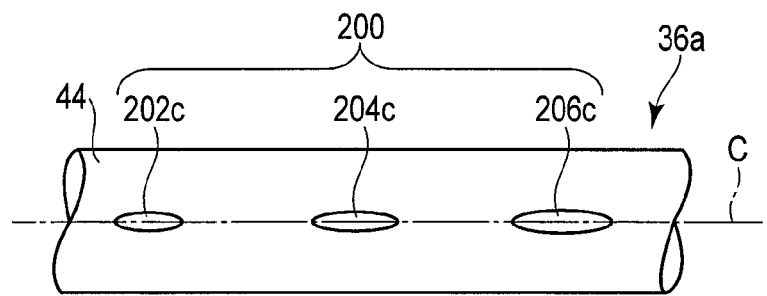
FIG. 16A is a schematic front view showing how elliptic depressions are formed in the outer circumferential surface of an outer tube of the flexible tubular portion in the insertion portion of the endoscope according to a fourth modification of the second embodiment.

As shown in FIG. 16A, depressions 202c, 204c, and 206c are not substantially circular, but are, for example, oval or elliptically shaped in the axial direction parallel to the central axis C. The sizes and depths of the depressions 202c, 204c, and 206c can be suitably changed.

Figure 16B:
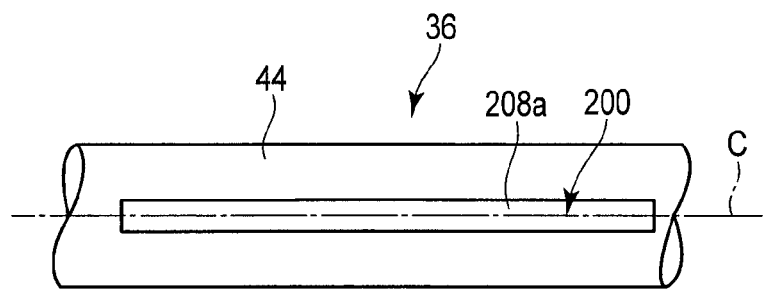
FIG. 16B is a schematic front view showing how a groove (depression) is formed in the outer circumferential surface of the outer tube parallel to the central axis.

As shown in FIG. 16B, a depression 208a is not circular, but is, for example, shaped into a groove parallel to the central axis C. That is, a proper length of the depression 208a is formed in a proper range of the flexible tubular portion 36. In this case, the degree of inhibiting the movement of the spiral tube 42 relative to the outer tube 44 can be steplessly adjusted by pressing a proper position in one depression 208a. The depression 208a of the outer tube 44 is not exclusively rectangular, and can be variously modified. For example, the depression 208a can be larger in circumferential width closer to the distal side, or larger in circumferential width closer to the proximal side.

Figure 16C:
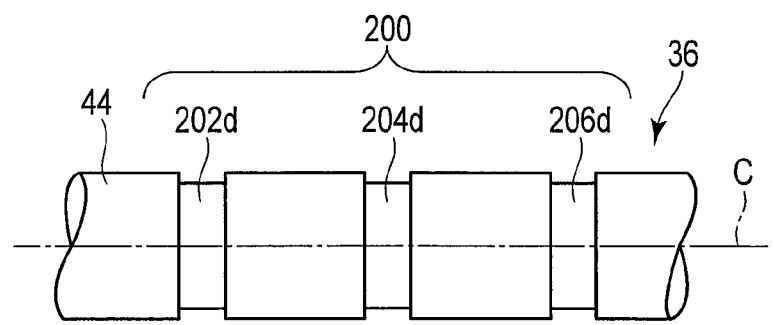
FIG. 16C is a schematic front view showing how depressions are formed in the outer circumferential surface of the outer tube in a circumferential direction that intersects at right angles with the central axis.

As shown in FIG. 16C, depressions 202d, 204d, and 206d are formed, for example, at proper intervals D in the entire circumferential direction that intersects at right angles with the central axis C. The axial widths of depressions 202d, 204d, and 206d can be suitably changed. Although not shown, adjacent depression may be formed with different depths. For example, the depth of the central depression 204d can be greater than the depth of the depression 202d closer to the distal side than the depression 204d, and smaller than the depth of the proximal-side depression 206d, and vice versa. The depths of the depressions 202d and 206d can be constant, and the depth of the central depression 204d can be greater or smaller than the depths of the depressions 202d and 206d. The depths can be thus properly set.

Figure 16D:
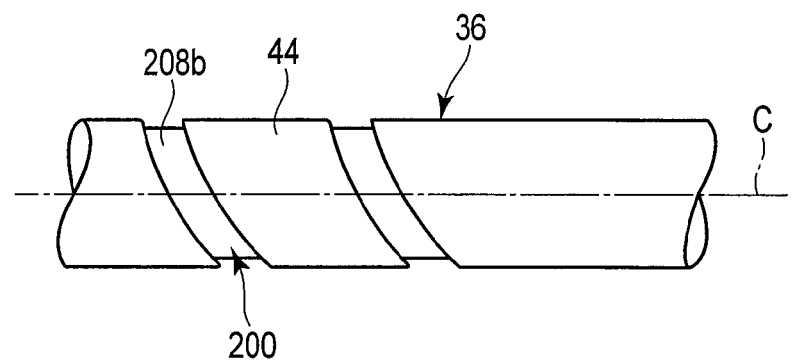
FIG. 16D is a schematic front view showing how a depression is formed in the outer circumferential surface of the outer tube spirally relative to the central axis.

As shown in FIG. 16D, a depression 208b is formed, for example, spirally relative to the central axis C. In this case, the degree of inhibiting the movement relative to the outer tube 44 can be steplessly adjusted by pressing a proper position in one depression 208b. The winding direction of the spiral of the depression 208b may be the same as or opposite to that of the sparsely wound portion 54b.

The spiral 208b is preferably continuously formed, or more than one spiral may be discontinuously formed.

[Fifth Modification]

Now, a fifth modification of the second embodiment is described with reference to FIG. 17.

Figure 17:
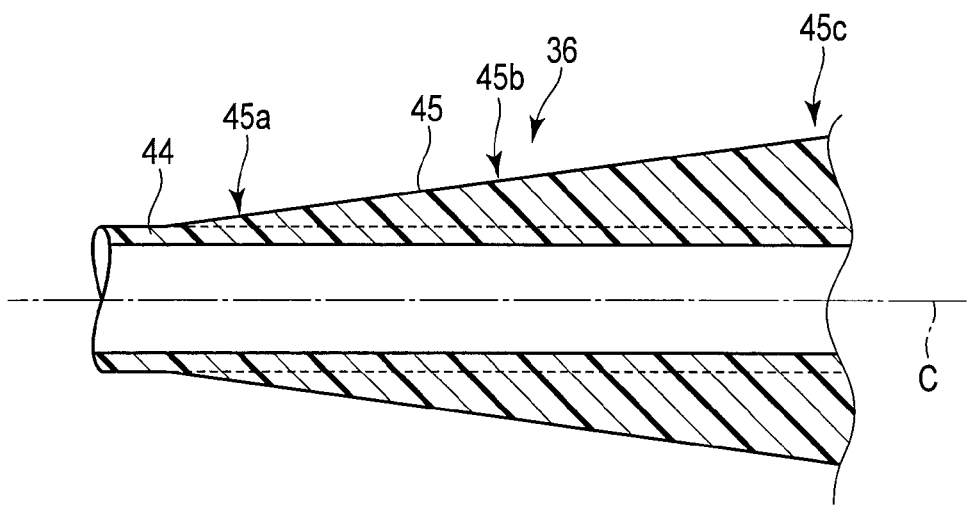
FIG. 17 is a schematic longitudinal sectional view showing how a thick portion which is thicker on the proximal side is formed in the outer tube of the flexible tubular portion of the insertion portion in the endoscope according to the fifth modification of the second embodiment.

The shape of a part of the outer tube 44 located outside the proximal-side sparsely wound portion 54b is shown in FIG. 17. The outer tube 44 has, on its outside, a thick portion (inhibiting portion) 45 which is formed to be thicker from the left side (distal side) to the right side (proximal side) in FIG. 17. That is, the thick portion 45 is formed to be thinner on the distal side including the position indicated by the sign 45a and thicker on the proximal side including the positions indicated by the signs 45b and 45c. Broken lines in FIG. 17 show a case where the thickness of the outer tube 44 is constant. The thick portion 45 is preferably formed so that its distal end is located closer to the proximal side, for example, about 200 mm to several hundred mm from the distal end (end coupled to the bending portion 34) of the outer tube 44 of the flexible tubular portion 36.

Thus, according to this modification, the thick portion 45 is formed to be thicker on the proximal side (e.g., the positions indicated by the signs 45b and 45c) than on the distal side indicated by the sign 45a. Therefore, more force is required to press the proximal side of the thick portion 45 of the outer tube 44 toward the central axis C to inhibit the movement of the sparsely wound portion 54b relative to the outer tube 44 than to press the distal side of the thick portion 45 of the outer tube 44 toward the central axis C to inhibit the movement of the sparsely wound portion 54b relative to the outer tube 44. That is, since the inhibiting portion (thick portion) 45 changes the thickness of the outer tube (outer layer) 44 along the longitudinal direction, the force to press the spiral tube 42 toward the central axis can be changed in accordance with the thickness when the same force F is applied from the outside of the outer tube 44 toward the central axis C. Thus, the degree of inhibiting the movement of the spiral tube 42 relative to the outer tube 44 can be suitably changed. In this case, the degree of inhibiting the movement of the sparsely wound portion 54b relative to the outer tube 44 can be steplessly adjusted by pressing a proper position in the thick portion 45.

It is also preferable that the thick portion 45 is formed separately from the outer tube 44 and that the thick portion 45 uses a flexible member removable from the outer tube 44. In this case, if the thick portion 45 is located at a proper position in the axial direction of the flexible tubular portion 36 of the insertion portion 12, the degree of inhibiting the movement of the sparsely wound portion 54b relative to the outer tube 44 can be steplessly adjusted.

[Sixth Modification]

Now, a sixth modification of the second embodiment is described with reference to FIG. 18A. It is naturally preferable that the flexible tubular portion 36 having ring members 222a, 224a, and 226a described below has the thick portion 45 described in the fifth modification.

Figure 18A:
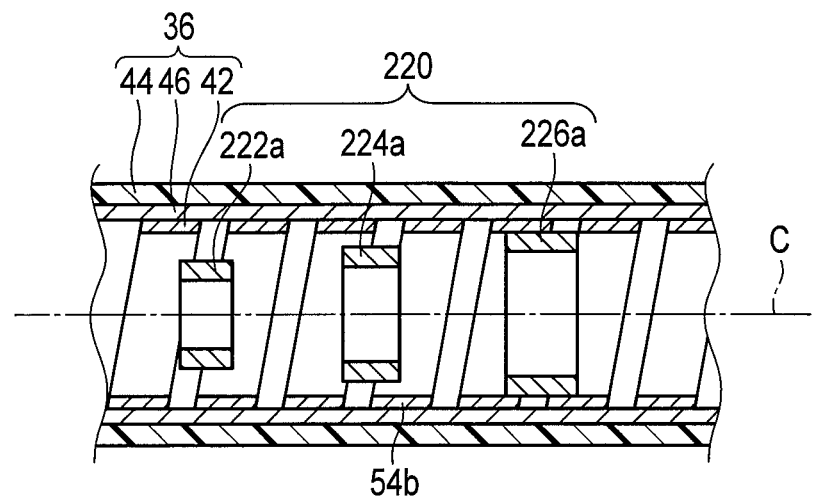
FIG. 18A is a schematic longitudinal sectional view showing how annular ring members which increase in outside diameter from the distal side toward the proximal side are arranged inside the spiral tube of the flexible tubular portion of the insertion portion in the endoscope according to a sixth modification of the second embodiment.

As shown in FIG. 18A, a support portion 220 is provided as an inhibiting portion inside the proximal-side sparsely wound portion 54b. The support portion 220 supports the inner circumferential surface of the spiral tube 42 at a proper diameter when a press force is applied from the outside of the outer tube 44 toward the central axis C. The support portion (inhibiting portion) 220 has multiple (here, three) annular ring members 222a, 224a, and 226a. These ring members 222a, 224a, and 226a are provided inside the proximal-side sparsely wound portion 54b of the spiral tube 42 around the central axis C. The ring members 222a, 224a, and 226a are preferably formed to have the same width in the direction along the central axis C. The outside diameter of the distal-side ring member 222a among the ring members 222a, 224a, and 226a is smaller than the outside diameters of the ring members 224a and 226a closer to the proximal side. The outside diameter of the ring member 224a is smaller than the outside diameter of the ring member 226a closer to the proximal side.

The ring members 222a, 224a, and 226a are preferably movable along the central axis C by the use of the above-mentioned lever adjusting portion 80 or cam ring adjusting portion 110 so that the distance therebetween is maintained.

The ring members 222a, 224a, and 226a are moved relative to the flexible tubular portion 36 along the central axis C to press the outer tube 44 outside the ring member 222a so that the ring member 222a is located at a proper position. In this case, the inside diameter of the mesh tube 46 inside the outer tube 44 and the inside diameter of the proximal-side sparsely wound portion 54b of the spiral tube 42 are reduced by the pressing of the outer tube 44. Thus, the inner circumferential surface of the sparsely wound portion 54b bumps into the outer circumferential surface of the ring member 222a. As a result, the movement of the sparsely wound portion 54b relative to the outer layer (the outer tube 44 and the mesh tube 46) is inhibited.

When the outer circumferential surface of the ring member 222a among the ring members 222a, 224a, and 226a is brought into close contact with the inner circumferential surface of the sparsely wound portion 54b, the deformation amount of the sparsely wound portion 54b needs to be increased to inhibit the movement of the sparsely wound portion 54b because the distal-side ring member 222a is smaller in outside diameter than the proximal-side ring members 224a and 226a. Therefore, when the inner circumferential surface of the sparsely wound portion 54b is brought into abutment with the distal-side ring member 222a, it is necessary to press the outer tube 44 toward the central axis C with a force greater than when the proximal-side ring members 224a and 226a are used, and thereby inhibit the movement of the sparsely wound portion 54b.

Thus, when the distal-side ring member 222a is used, a stronger force is used for holding. Therefore, the movement amount of the sparsely wound portion 54b toward the central axis C is greater, and the effect of inhibiting the movement of the proximal-side sparsely wound portion 54b relative to the outer layer can be higher.

The outside diameter of the most proximal ring member 226a slightly larger than the outside diameter of the most distal ring member 222a is slightly smaller than the inside diameter of the sparsely wound portion 54b. Thus, since the proximal ring member 226a is larger in outside diameter than the ring members 222a and 224a closer to the distal side, it is possible to press the outer tube 44 toward the central axis C with less force to inhibit the movement of the sparsely wound portion 54b when the outer circumferential surface of the ring member 226a is brought into close contact with the inner circumferential surface of the sparsely wound portion 54b.

In this modification as well, the ring members 222a, 224a, and 226a are only used, and no particular maintenance of the flexible tubular portion 36 is therefore needed.

[Seventh Modification]

Now, a seventh modification of the second embodiment is described with reference to FIG. 18B.

Figure 18B:
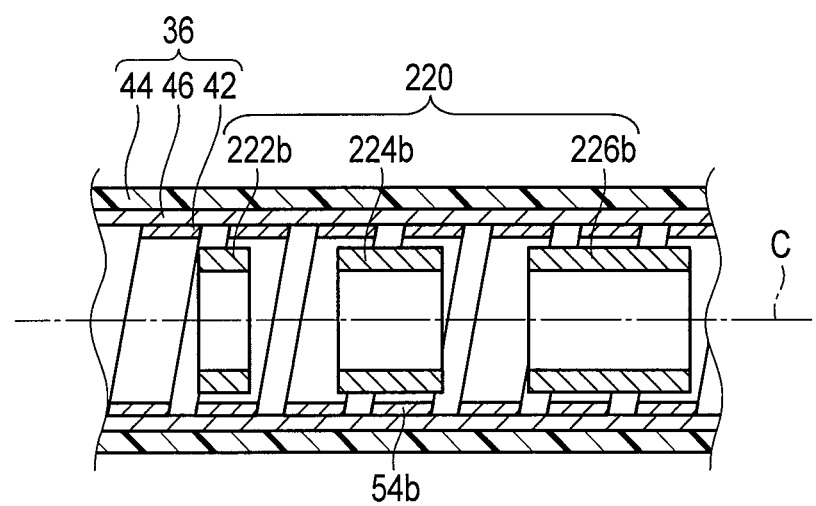
FIG. 18B is a schematic longitudinal sectional view showing how annular ring members which gradually increase in axial width from the distal side toward the proximal side are arranged inside the spiral tube of the flexible tubular portion of the insertion portion in the endoscope according to a seventh modification of the second embodiment.

As shown in FIG. 18B, the support portion 220 is provided inside the proximal-side sparsely wound portion 54b. The support portion 220 has multiple (here, three) annular ring members 222b, 224b, and 226b. These ring members 222b, 224b, and 226b are provided inside the proximal-side sparsely wound portion 54b of the spiral tube 42 around the central axis C. The outside diameters of the ring members 222b, 224b, and 226b are formed to be substantially the same, and formed to be slightly smaller than the inside diameter of the sparsely wound portion 54b. The ring members 222b, 224b, and 226b are different in width in the direction along the central axis C. The width of the distal-side ring member 222b among the ring members 222b, 224b, and 226b is smaller than the widths of the ring members 224b and 226b closer to the proximal side. The width of the ring member 224b is smaller than the width of the ring member 226b closer to the proximal side.

The ring members 222b, 224b, and 226b are preferably movable along the central axis C by the use of the above-mentioned lever adjusting portion 80 or cam ring adjusting portion 110 so that the distance therebetween is maintained.

The ring members 222b, 224b, and 226b are moved relative to the flexible tubular portion 36 along the central axis C to press the outer tube 44 outside the ring member 222b toward the central axis C so that the ring member 222b is located at a proper position. In this case, the inside diameter of the mesh tube 46 inside the outer tube 44 and the inside diameter of the proximal-side sparsely wound portion 54b of the spiral tube 42 are reduced by the pressing of the outer tube 44. Thus, the inner circumferential surface of the sparsely wound portion 54b bumps into the outer circumferential surface of the ring member 222b, and the movement of the sparsely wound portion 54b relative to the outer tube 44 is inhibited.

When the outer circumferential surface of the distal-side ring member 222b among the ring members 222b, 224b, and 226b is brought into close contact with the inner circumferential surface of the sparsely wound portion 54b, the area of contact with the inner circumferential surface of the sparsely wound portion 54b is small because the distal-side ring member 222b is smaller in width than the proximal-side ring members 224b and 226b. Therefore, when the sparsely wound portion 54b is held to the distal-side ring member 222b, it is necessary to press the outer tube 44 toward the central axis C with a force greater than in the case of the proximal-side ring members 224b and 226b, and thereby inhibit the movement of the sparsely wound portion 54b.

Since the proximal-side ring member 226b is greater in width than the ring members 222b and 224b closer to the distal side, the area of contact can be larger when the outer circumferential surface of the ring member 226b is brought into close contact with the inner circumferential surface of the sparsely wound portion 54b. Therefore, when the outside of the most proximal ring member 226b is pressed, the movement of the sparsely wound portion 54b relative to the outer tube 44 can be inhibited if the outer tube 44 is pressed toward the central axis C with less force.

[Seventh Modification]

Now, an eighth modification of the second embodiment is described with reference to FIG. 18C.

Figure 18C:
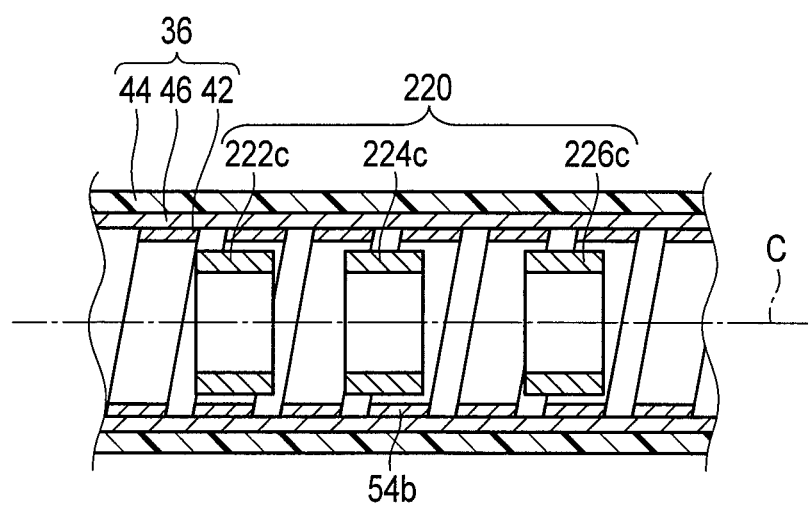
FIG. 18C is a schematic longitudinal sectional view showing how annular ring members having outer circumferential surfaces which gradually increase in friction coefficient from the distal side toward the proximal side are arranged inside the spiral tube of the flexible tubular portion of the insertion portion in the endoscope according to an eighth modification of the second embodiment.

As shown in FIG. 18C, the support portion 220 is provided inside the proximal-side sparsely wound portion 54b. The support portion 220 has multiple (here, three) annular ring members 222c, 224c, and 226c. These ring members 222c, 224c, and 226c are provided inside the proximal-side sparsely wound portion 54b of the spiral tube 42 around the central axis C. The outside diameters of the ring members 222c, 224c, and 226c are formed to be substantially the same, and formed to be slightly smaller than the inside diameter of the sparsely wound portion 54b. The widths of the ring members 222c, 224c, and 226c in the direction along the central axis C are also formed to be substantially the same. However, the frictional coefficient of the distal-side ring member 222c among the ring members 222c, 224c, and 226c is lower than the frictional coefficient of the ring members 224c and 226c closer to the proximal side. The frictional coefficient of the ring member 224c is lower than the frictional coefficient of the ring member 226c closer to the proximal side.

The ring members 222c, 224c, and 226c are preferably movable along the central axis C by the use of the above-mentioned lever adjusting portion 80 or cam ring adjusting portion 110 so that the distance therebetween is maintained.

The ring members 222c, 224c, and 226c are moved relative to the flexible tubular portion 36 along the central axis C to press the outer tube 44 outside the ring member 222c toward the central axis C so that the ring member 222c is located at a proper position. In this case, the inside diameter of the mesh tube 46 inside the outer tube 44 and the inside diameter of the proximal-side sparsely wound portion 54b of the spiral tube 42 are reduced by the pressing of the outer tube 44. Thus, the inner circumferential surface of the sparsely wound portion 54b bumps into the outer circumferential surface of the ring member 222c, and the movement of the sparsely wound portion 54b relative to the outer tube 44 is inhibited.

When the outer circumferential surface of the distal-side ring member 222c among the ring members 222c, 224c, and 226c is brought into close contact with the inner circumferential surface of the sparsely wound portion 54b, the frictional coefficient of the distal-side ring member 222c is lower than the frictional coefficients of the proximal-side ring members 224c and 226c. Thus, it is necessary to press the outer tube 44 toward the central axis C with greater force to inhibit the movement of the sparsely wound portion 54b.

Since the proximal-side ring member 226c is higher in frictional coefficient than the ring members 224a and 226a closer to the distal side, an inhibiting force to inhibit the movement of the sparsely wound portion 54b relative to the outer tube 44 can be greater when the outer circumferential surface of the ring member 226a is brought into close contact with the inner circumferential surface of the sparsely wound portion 54b. Therefore, when the outside of the most proximal ring member 226c is pressed, the movement of the sparsely wound portion 54b relative to the outer tube 44 can be inhibited if the outer tube 44 is pressed toward the central axis C with less force.

Third Embodiment

Now, a third embodiment is described with reference to FIG. 19A. This embodiment is a modification of the first and second embodiments, and the same components as the components described in the first and second embodiments are provided with the same reference signs and are not described in detail. It should be understood that the contents described in the first embodiment including its modifications and the contents described in the second embodiment including its modifications can be combined as described above.

In the example described according to this embodiment, the user of the endoscope 10 adjusts, as an inhibiting portion, the distance (space) between the linear members 42a of the sparsely wound portion 54b of the flexible tubular portion 36 of the insertion portion 12 to inhibit the movement of the sparsely wound portion 54b.

As shown in FIG. 19A, a distance adjusting portion (inhibiting portion) 250 is provided between the proximal end of the proximal-side sparsely wound portion 54b of the spiral tube 42, that is, the proximal end of the spiral tube 42, and the operation portion 14. The distance adjusting portion 250 adjusts the space between the linear members 42a of the sparsely wound portions 54a and 54b, that is, the distance between the linear members 42a to adjust the hardness of the flexible tubular portion 36.

The distance adjusting portion 250 has a movable member (inhibiting member) 252 fixed to the proximal end of the proximal-side sparsely wound portion 54b of the spiral tube 42, that is, the proximal end of the spiral tube 42, and a guide 254 which is formed in, for example, the inner circumferential surface of the mouth ring 38b of the protection hood 24 and which moves the movable member 252 in a predetermined range. The guide 254 is preferably formed parallel to the central axis C of the insertion portion 12.

The movable member 252 has, for example, a cylindrical member 262, and a protruding portion 264 protruding diametrically outwardly from the cylindrical member 262. The cylindrical member 262 is fixed to the proximal end of the spiral tube 42. The protruding portion 264 is disposed slidably over the guide 254 formed on the inner circumferential surface of the protection hood 24.

Here, the movable member 252 can be moved parallel to the central axis C by the use of the above-mentioned lever adjusting portion 80 or cam ring adjusting portion 110.

For example, if the movable member 252 is located on the distal side indicated by solid lines in FIG. 19A, the space between the linear members 42a of the sparsely wound portions 54a and 54b (the sparsely wound portion 54a is not shown in FIG. 19A) is reduced. Thus, if the movable member 252 is locked with the protection hood 24, the sparsely wound portions 54a and 54b can be difficult to move relative to the outer tube 44, and the movement can be inhibited. Therefore, the flexible tubular portion 36 can be harder and stronger.

On the other hand, if the movable member 252 is moved from the position indicated by the solid lines in FIG. 19A to a position indicated by broken lines, the space between the linear members 42a of the sparsely wound portions 54a and 54b is expanded, and the sparsely wound portions 54a and 54b can be more easily moved relative to the outer tube 44. As a result, the flexible tubular portion 36 becomes more flexible and less strong.

In this way, the movability of the linear members 42a of the sparsely wound portions 54a and 54b along the central axis C can be changed by adjusting the distance between the linear members 42a. Thus, the hardness of the flexible tubular portion 36 can be easily adjusted.

In this embodiment as well, the movable member 252 is only used as the inhibiting member, and no particular maintenance is therefore needed.

[First Modification]

Now, a first modification of the third embodiment is described with reference to FIG. 19B.

Figure 19B:
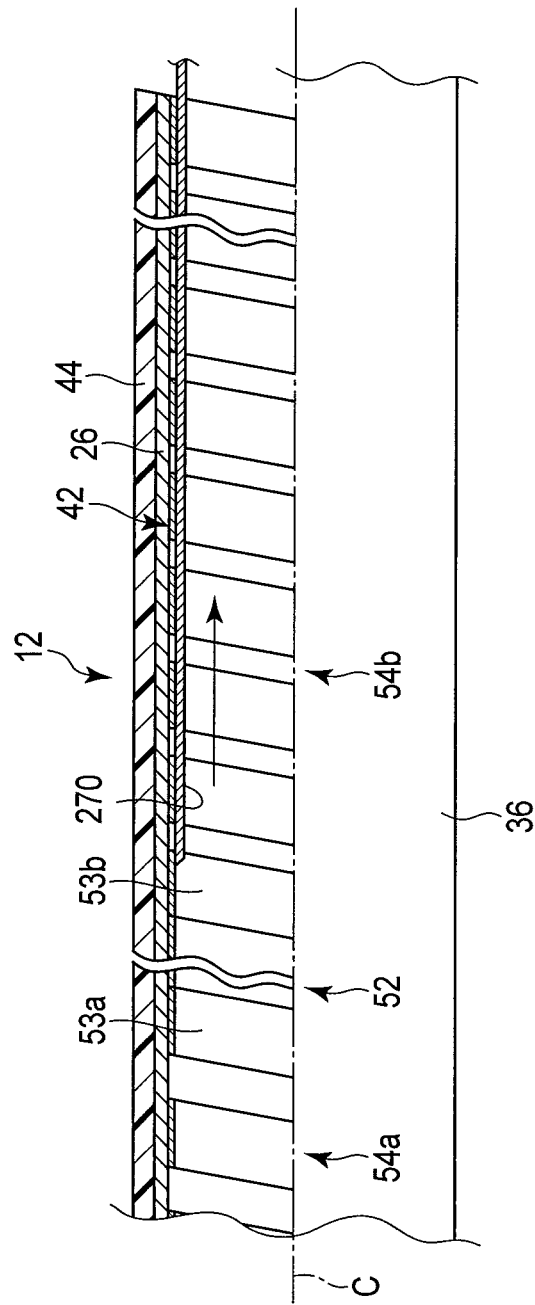
FIG. 19B is a schematic partial longitudinal sectional view showing the flexible tubular portion having the three-layer structure of the insertion portion according to a first modification of the third embodiment.

As shown in FIG. 19B, a flexible traction member (inhibiting portion) 270 such as a wire is inserted through the spiral tube 42 from the proximal end of the spiral tube 42 to the proximal end of the closely wound portion 52. The distal end of the traction member 270 is fixed to the linear member 42a at the proximal end of the closely wound portion 52.

The proximal end of the traction member 270 can be moved parallel to the central axis C by the use of, for example, the above-mentioned lever adjusting portion 80 or cam ring adjusting portion 110.

When the traction member 270 is loosened, the space between the linear members 42a of the distal-side sparsely wound portion 54a is substantially the same as the space between the linear members 42a of the proximal-side sparsely wound portion 54b. As tension is applied to the traction member 270, the space between the linear members 42a of the distal-side sparsely wound portion 54a is widened, and the space between the linear members 42a of the proximal-side sparsely wound portion 54b is narrowed. Thus, the traction member 270 functions as a distance adjusting portion to adjust the distance between the linear members 42a in the direction along the central axis C. Therefore, the flexible tubular portion 36 is flexible and less strong at the position corresponding to the distal-side sparsely wound portion 54a, and is hard and strong at the position corresponding to the proximal-side sparsely wound portion 54b.

The following can be said according to the embodiments described above.

An endoscopic flexible tubular portion having a central axis includes a spiral tube including, along the longitudinal direction of the central axis, a closely wound portion to which an initial tension is applied, and sparsely wound portions provided on the distal side and the proximal side of the closely wound portion, an outer layer covering the outside of the spiral tube, and an inhibiting portion which inhibits the movement of at least some of the sparsely wound portions relative to the outer layer in the longitudinal direction of the spiral tube.

Since the length of the outer layer does not change when the spiral tube is bent, the linear members of the spiral tube in the direction along the central axis come closer to or away from each other so that a constant overall length of the spiral tube is maintained. According to the embodiments described above, the inhibiting portion which inhibits the movement of the sparsely wound portions relative to the outer layer is provided. The inhibiting portion functions so that the range in which the linear members in the direction along the central axis come closer to or away from each other is smaller than when the movement between the linear members is not inhibited in the sparsely wound portions. That is, this is the same as or close to the reduction of the length of the spiral tube. Thus, the spring characteristics of the spiral tube can be changed by the inhibiting portion, and an adjustment (adjustment of the hardness of the flexible tubular portion) can be made so that the flexible tubular portion will be hard (strong) and difficult to bend or will be flexible (less strong) and easy to bend. According to the embodiments described above, the movement of the spiral tube on the distal side is not inhibited (restricted) as compared to the position where the movement of the spiral tube is inhibited, so that there is no anisotropy in the circumferential direction, and the same flexibility and isotropy are also provided in different directions.

It is preferable that the inhibiting portion is provided at least inside the spiral tube, outside the spiral tube, or in the flexible tubular portion and that the inhibiting portion includes an inhibiting member which inhibits the movement of at least some of the sparsely wound portions relative to the outer layer in the longitudinal direction of the spiral tube.

The movement of the sparsely wound portion can be easily inhibited by the use of the inhibiting member.

It is preferable that the outer layer has a thickness in the diametrical direction of the central axis and that the inhibiting portion changes the thickness of the outer layer along the longitudinal direction.

Since the inhibiting portion changes the thickness of the outer layer along the longitudinal direction, a force to press the spiral tube toward the central axis is changed in accordance with the thickness, and the degree of inhibiting the movement of the spiral tube relative to the outer layer can be suitably changed.

It is preferable that the inhibiting portion has at least one ring member inside the spiral tube.

When the outer layer is pressed toward the central axis by the ring member, the movement of the spiral tube can be inhibited by the spiral tube and the outer circumferential surface of the ring member.

It is preferable that the inhibiting portion has, in the outer surface of the outer layer, at least one depression which is configured to deform the spiral tube toward the central axis through the outer layer when the outer layer is pressed toward the central axis.

When the outer layer is pressed toward the central axis, the movement of the spiral tube relative to the outer layer can be effectively inhibited because of the presence of the depression where the thickness of the outer layer is reduced.

It is preferable that the spiral tube is formed by a linear member and that the inhibiting portion has a distance adjusting portion which changes the distance between the linear members of the sparsely wound portions in a direction along the longitudinal direction of the central axis.

The movability of the linear members along the central axis can be changed by adjusting the distance between the linear members. Thus, the hardness of the flexible tubular portion can be adjusted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tubular portion for an endoscope having a central axis, the flexible tubular portion comprising:
    a spiral tube including, along the longitudinal direction of the central axis, a closely wound portion to which an initial tension is applied, and sparsely wound portions provided on the distal side and the proximal side of the closely wound portion,
    an outer layer covering the outside of the spiral tube; and
    an inhibiting portion which inhibits the movement of at least a part of the sparsely wound portions relative to the outer layer in the longitudinal direction of the spiral tube.

2. The flexible tubular portion according to claim 1, wherein the inhibiting portion includes an inhibiting member which is provided at least one inside the spiral tube, outside the spiral tube, and in the flexible tubular portion and which inhibits the movement of the at least the part of the sparsely wound portions relative to the outer layer in the longitudinal direction of the spiral tube.

3. The flexible tubular portion according to claim 2, wherein the inhibiting member is located at a position corresponding to the sparsely wound portion provided on the proximal side of the closely wound portion.

4. The flexible tubular portion according to claim 1, wherein the inhibiting portion includes a second helical tube which is provided outside the sparsely wound portion provided on the proximal side of the closely wound portion.

5. The flexible tubular portion according to claim 4, wherein the second helical tube moves outside the spiral tube along the longitudinal direction of the central axis in accordance with an external operation.

6. The flexible tubular portion according to claim 1, wherein the inhibiting portion is configured to steplessly adjust the degree of inhibiting the movement of the at least the part of the sparsely wound portions relative to the outer layer in the longitudinal direction of the spiral tube.

7. The flexible tubular portion according to claim 1, wherein
    the spiral tube and the outer layer are configured to be deformed so that the inside diameters thereof are reduced toward the central axis when pressed toward the central axis from the outside thereof,
    the outer layer has a thickness in the diametrical direction of the central axis, and
    the inhibiting portion is a portion which is configured to change the thickness of the outer layer along the longitudinal direction.

8. The flexible tubular portion according to claim 1, wherein
    the spiral tube and the outer layer are configured to be deformed so that the inside diameters thereof are reduced toward the central axis when pressed toward the central axis from the outside thereof, and
    the inhibiting portion includes, inside the spiral tube, at least one ring member, an outer circumferential surface of the ring member contacting contacts the inner circumferential surface of the spiral tube reduced in inside diameter.

9. The flexible tubular portion according to claim 1, wherein
    the spiral tube and the outer layer are configured to be deformed so that the diameters thereof are increased or reduced when pressed by a force in a diametrical direction around the central axis, and
    the inhibiting portion includes a circularly expanding balloon which is provided to contact the surface of the spiral tube or the outer layer, and a tube which lets outside air in and out of the balloon.

10. The flexible tubular portion according to claim 1, wherein
    the spiral tube and the outer layer are configured to be deformed so that the diameters thereof are increased or reduced when pressed by a force in a diametrical direction around the central axis, and
    the inhibiting portion includes a catching portion movable along the central axis, the catching portion including a press member which presses the outside of the outer layer in the direction of the central axis, and a holder which holds the press member and which fastens and loosens the press member.

11. The flexible tubular portion according to claim 1, wherein the inhibiting portion includes, in the outer surface of the outer layer, at least one depression which is configured to deform the spiral tube toward the central axis through the outer layer when the outer layer is pressed toward the central axis.

12. The flexible tubular portion according to claim 11, wherein the depression is configured to adjust the degree of inhibiting the movement of the at least the part of the sparsely wound portions relative to the outer layer in the longitudinal direction of the spiral tube in accordance with a position in the depression pressed toward the central axis.

13. The flexible tubular portion according to claim 11, wherein
    more than one depression is provided, and
    one of the depressions and another are formed so that the degree of inhibiting the movement of the at least the part of the sparsely wound portions relative to the outer layer in the longitudinal direction of the spiral tube varies when the depressions are pressed toward the central axis.

14. The flexible tubular portion according to claim 11, further including a press member which is provided outside the outer layer and which is configured to press the outer layer toward the central axis.

15. The flexible tubular portion according to claim 14, wherein the press member includes a protrusion which presses the depression.

16. The flexible tubular portion according to claim 1, wherein
    the spiral tube and the outer layer are configured to be deformed so that the diameters thereof are increased or reduced when pressed by a force in a diametrical direction around the central axis, and the inhibiting portion includes a power supply, and an actuator which is driven by the application of electric energy from the power supply and which is configured to press the inner circumferential surface of the spiral tube.

17. The flexible tubular portion according to claim 1, wherein the spiral tube is formed by a linear member, and the inhibiting portion includes a distance adjusting portion which is configured to change the distance between parts of the linear member of the sparsely wound portions in a direction along the longitudinal direction of the central axis.

18. The flexible tubular portion according to claim 17, wherein the distance adjusting portion includes a traction member having one end fixed to the spiral tube and the other end configured to be pulled along the longitudinal direction of the central axis.

19. The flexible tubular portion according to claim 17, wherein the distance adjusting portion includes a movable member which is fixed to the spiral tube and which is movable along the longitudinal direction of the central axis.

20. An endoscope comprising the flexible tubular portion according to claim 1.

\* \* \* \* \*